US008399670B2

(12) United States Patent
Rybtchinski et al.

(10) Patent No.: US 8,399,670 B2
(45) Date of Patent: Mar. 19, 2013

(54) SELECTIVE BROMINATION OF PERYLENE DIIMIDES AND DERIVATIVES THEREOF UNDER MILD CONDITIONS

(75) Inventors: Boris Rybtchinski, Tel Aviv (IL); Paramasivan Rajasingh, Sonaganvilai (IN); Elijah Shirman, Rehovot (IL)

(73) Assignee: Yeda Research and Development Co.Ltd, Rehovot (IL)

( * ) Notice: Subject to any disclaimer, the term of this patent is extended or adjusted under 35 U.S.C. 154(b) by 365 days.

(21) Appl. No.: 12/599,292

(22) PCT Filed: May 6, 2008

(86) PCT No.: PCT/IL2008/000621
§ 371 (c)(1),
(2), (4) Date: Jun. 22, 2010

(87) PCT Pub. No.: WO2008/139452
PCT Pub. Date: Nov. 20, 2008

(65) Prior Publication Data
US 2010/0261901 A1    Oct. 14, 2010

Related U.S. Application Data

(60) Provisional application No. 60/924,327, filed on May 9, 2007.

(51) Int. Cl.
*C07D 471/08*    (2006.01)
*C07D 471/02*    (2006.01)
(52) U.S. Cl. .......................................... 546/37; 546/36
(58) Field of Classification Search ................ 546/37, 546/36
See application file for complete search history.

(56) References Cited

U.S. PATENT DOCUMENTS

| | | | |
|---|---|---|---|
| 6,143,905 | A | 11/2000 | Böhm et al. |
| 6,184,378 | B1 | 2/2001 | Böhm et al. |
| 6,326,494 | B1 | 12/2001 | Böhm et al. |
| 2005/0176970 | A1 | 8/2005 | Marks et al. |

FOREIGN PATENT DOCUMENTS

| | | |
|---|---|---|
| CN | 1706842 A * | 12/2005 |
| WO | WO 97/22607 | 6/1997 |
| WO | WO 2009/118742 | 10/2009 |

OTHER PUBLICATIONS

Addicott C, Oesterling I, Yamamoto T, Müllen K, Stang PJ., "Synthesis of a bis(pyridyl)-substituted perylene diimide ligand and incorporation into a supramolecular rhomboid and rectangle via coordination driven self-assembly," J Org Chem. Feb. 4, 2005;70(3):797-801.
Becke A.D., "Density-functional thermochemistry. III. The role of exact exchange," J. Chem. Phys., 1993, 98 (7), pp. 5648-5652.
Breeze A.J., Salomon A., Ginley D.S., Gregg B.A., Tillmann H., Hörhold H-H., "Polymer—perylene diimide heterojunction solar cells," Appl. Phys. Lett., 2002, 81, 3085.
Demmig S., Langhals H., "Easily soluble and photostable perylene fluorescent dyes," Chemische Berichte, 1988, vol. 121 Issue 2, pp. 225-230.
Dimitrakopoulos C.D., Malenfant P.R.L., "Organic thin film transistors for large area electronics," Advanced Materials, 2002, 14, pp. 99-117.
Ebeid E.Z.M., Ei-Daly S.A., Langhals H., "Emission characteristics and photostability of N,N'-bis(2,5-di-tert-butylphenyl)-3,4:9,10-perylenebis(dicarboximide)," Journal of physical chemistry, 1988, vol. 92, No. 15, pp. 4565-4568.
Ego C., Marsitzky D., Becker S., Zhang J., Grimsdale A.C., Müllen K., MacKenzie J.D., Silva C., Friend R. H., J. Am. Chem. Soc., 2003, 125, 437.
Fan L., Xu Y., Tian H., "1,6-Disubstituted perylene bisimides: concise synthesis and characterization as near-infrared fluorescent dyes," Tetrahedron Letters, vol. 46, Issue 26, Jun. 27, 2005, pp. 4443-4447.
Jones B.A., Ahrens M.J., Yoon M.H., Facchetti A., Marks T.J., Wasielewski M.R., "High-Mobility Air-Stable n-Type Semiconductors with Processing Versatility: Dicyanoperylene-3,4:9,10-bis(dicarboximides)," Angew. Chem. Int. Ed. 2004, 43, 6363-6366.
Langhals H., "Control of the Interactions in Multichromophores: Novel Concepts. Perylene Bis-imides as Components for Larger Functional Units," Helvetica Chimica Acta, 2005 vol. 88, Issue 6, pp. 1309-1343.
Langhals H., "Synthesis of highly pure perylene fluorescent dyes in large scale amounts-specific preparation of atropisomers," Chemische Berichte, 1985, vol. 118, No. 11, pp. 4641-4645.
Langhals, H., Kirner S., "Novel Fluorescent Dyes by the Extension of the Core of Perylenetetracarboxylic Bisimides," European Journal of Organic Chemistry, 2000, vol. 2000, Iss. 2, pp. 365-380.
Langhals H, Krotz O, Polborn K, Mayer P, "A novel fluorescent dye with strong, anisotropic solid-state fluorescence, small stokes shift, and high photostability," Angew Chem Int Ed Engl. Apr. 15, 2005;44(16):2427-8.
Li Y, Li Y, Li J, Li C, Liu X, Yuan M, Liu H, Wang S, "Synthesis, Characterization, and Self-Assembly of Nitrogen-Containing Heterocoronenetetracarboxylic Acid Diimide Analogues: Photocyclization of N-Heterocycle-Substituted Perylene Bisimides," Chem. Eur. J., 2006, 12, pp. 8378-8385.
Li Y, Li H, Li Y, Liu H, Wang S, He X, Wang N, Zhu D., "Energy transfer switching in a bistable molecular machine," Org Lett. Oct. 27, 2005;7(22):4835-8.
Li X., Sinks L.E., Rybtchinski B., Wasielewski M.R., "Ultrafast Aggregate-to-Aggregate Energy Transfer within Self-assembled Light-Harvesting Columns of Zinc Phthalocyanine Tetrakis(Perylenediimide)," J. Am. Chem. Soc. 2004, 126, 10810-10811.
Li Y., Wang N., He X., Wang S., Liu H., Li Y., Li X., Zhuang J., Zhu D., "Synthesis and characterization of ferrocene-perylenetetracarboxylic diimide—fullerene triad," Tetrahedron, vol. 61, Issue 6, Feb. 7, 2005, pp. 1563-1569.
Locklin J., Li D., Mannsfeld S.C.B., Borkent E-J., Meng H., Advincula R., Bao Z., "Organic Thin Film Transistors Based on Cyclohexyl-Substituted Organic Semiconductors," Chem. Mater., 2005, 17 (13), pp. 3366-3374.
Peng C., Ayala P.Y., Schlegel H.B., Frisch M.J., "Using redundant internal coordinates to optimize equilibrium geometries and transition states," Journal of Computational Chemistry, 1996, vol. 17 Issue 1, pp. 49-56.

(Continued)

*Primary Examiner* — Charanjit Aulakh
(74) *Attorney, Agent, or Firm* — Pearl Cohen Zedek Latzer, LLP; Mark S. Cohen

(57) ABSTRACT

The present invention is directed to novel process for the preparation of regioselective perylenediimides derivatives, specifically mono and dibrominated derivatives.

12 Claims, 18 Drawing Sheets

OTHER PUBLICATIONS

Prathapan S., Yang S.I., Seth J., Miller M.A., Bocian D.F., Holten D., Lindsey J.S., "Synthesis and Excited-State Photodynamics of Perylene—Porphyrin Dyads. 1. Parallel Energy and Charge Transfer via a Diphenylethyne Linker," J. Phys. Chem. B, 2001, 105 (34), pp. 8237-8248.

Qu J., Pschirer N.G., Liu D., Stefan A., De Schryver F.C., Mullen K., "Dendronized perylenetetracarboxdiimides with peripheral triphenylamines for intramolecular energy and electron transfer," Chem. Eur. J., 2004, 10, 528-537.

Röger, C.; Müller, M. G.; Lysetska, M.; Miloslavina, Y.; Holzwarth, A. R.; Würthner, F. J. Am. Chem. Soc. 2006, 128, 6542-6543.

Rybtchinski B., Sinks L.E., Wasielewski M.R., "Combining Light-Harvesting and Charge Separation in a Self-Assembled Artificial Photosynthetic System Based on Perylenediimide Chromophores," J. Am. Chem. Soc., 2004, 126 (39), pp. 12268-12269.

Sautter A., Kaletaş B.K., Schmid D.G., Dobrawa R., Zimine M., Jung G., van Stokkum I.H., De Cola L., Williams R.M., Würthner F., "Ultrafast Energy-Electron Transfer Cascade in a Multichromophoric Light-Harvesting Molecular Square," J. Am. Chem. Soc., 2005, 127 (18), pp. 6719-6729.

Schlegel H.B., "Optimization of equilibrium geometries and transition structures," Journal of Computational Chemistry, 1982, vol. 3 Iss. 2, pp. 214-218.

Schmidt-Mende L., Fechtenkötter A., Müllen K., Moons E., Friend R.H., MacKenzie J.D., "Self-Organized Discotic Liquid Crystals for High-Efficiency Organic Photovoltaics," Science Aug. 10, 2001: vol. 293. No. 5532, pp. 1119-1122.

Shin W.S., Jeong H-H., Kim M-K., Jin S-H., Kim M-R., Lee J-K., Lee J.W., Gal Y-S., "Effects of functional groups at perylene diimide derivatives on organic photovoltaic device application," J. Mater. Chem., 2006, 16, 384-390.

Struijk C.W., Sieval A.B., Dakhorst J.E.J., van Dijk M., Kimkes P., Koehorst R.B.M., Donker H., Schaafsma T.J., Picken S.J., van de Craats A.M., Warman J.M., Zuilhof H., Sudhölter E.J.R., "Liquid Crystalline Perylene Diimides: Architecture and Charge Carrier Mobilities," J. Am. Chem. Soc., 2000, 122 (45), pp. 11057-11066.

Wang W., Wan W., Zhou H-H., Niu S., Li A.D.Q., "Alternating DNA and π-Conjugated Sequences. Thermophilic Foldable Polymers," J. Am. Chem. Soc., 2003, 125 (18), pp. 5248-5249.

Wasielewski M.R., "Energy, Charge, and Spin Transport in molecules and Self-Assembled Nanostructures Inspired by Photosynthesis," J. Org. Chem., 2006, 71, pp. 5051-5066.

Würthner F., "Perylene bisimide dyes as versatile building blocks for functional supramolecular architectures," Chemical communications 2004, No. 14, pp. 1564-1579.

Würthner F., Stepanenko V., Chen Z., Saha-Möer C.R., Kocher N., Stalke D., "Preparation and Characterization of Regioisomerically Pure 1,7-Disubstituted Perylene Bisimide Dyes," J. Org. Chem. 2004, 69, 7933-7939.

Würthner F., You C.C., Saha-Möller C.R., "Metallosupramolecular squares: from structure to function," Chem. Soc. Rev., 2004, 33, pp. 133-146.

Xiao S, El-Khouly ME, Li Y, Gan Z, Liu H, Jiang L, Araki Y, Ito O, Zhu D., "Dyads and triads containing perylenetetracarboxylic diimide and porphyrin: efficient photoinduced electron transfer elicited via both excited singlet states," J Phys Chem B. Mar. 3, 2005;109(8):3658-67.

Yakimov A., Forrest S.R., "High photovoltage multiple-heterojunction organic solar cells incorporating interfacial metallic nanoclusters," Appl. Phys. Lett., 2002, 80, 1667.

Yoo B., Jung T., Basu D., Dodabalapur A., Jones B.A., Facchetti A., Wasielewski M.R., Marks T.J., "High-mobility bottom-contact n-channel organic transistors and their use in complementary ring oscillators," Appl. Phys. Lett., 2006, 88, 082104.

You CC, Hippius C, Grüne M, Würthner F., "Light-harvesting metallosupramolecular squares composed of perylene bisimide walls and fluorescent antenna dyes," Chemistry. Sep. 25, 2006;12(28):7510-9.

Zang L., Liu R., Holman M.W., Nguyen K.T., Adams D.M., "A Single-Molecule Probe Based on Intramolecular Electron Transfer," J. Am. Chem. Soc., 2002, 124 (36), pp. 10640-10641.

Zhao Y., Wasielewski M.R., "3,4:9,10-Perylenebis(dicarboximide) chromophores that function as both electron donors and acceptors," Tetrahedron Letters, vol. 40, Iss. 39, 1999, pp. 7047-7050.

Zollinger H., (2003). ColorChemistry. 3rd ed. Verlag Helvetica Chimica Acta, Züurich, Wiley-VCH, Weinheim.

International Search Report of International application No. PCT/IL08/00621 dated Nov. 10. 2008.

European Search Report PCT/IL2008000621. Dated Jun. 30, 2011.

Fan et al. "1,6-Disubstituted perylene bisimides: concise synthesis and characterization as near-infrared fluorescent dyes" (2005).

Langhals & Kirner. "Novel Fluorescent Dyes by the Extension of the Core of Perylenetetracarboxylic Bisimides" Eur. J. Org. Chem, 365-380, (2000).

Rajasingh et al. "Selective Bromination of Perylene Diimides under Mild Conditions" J. Org. Chem., 72, 5973-5979, (2007).

* cited by examiner

SELECTIVE BROMINATION OF PERYLENE DIIMIDES AND DERIVATIVES THEREOF UNDER MILD CONDITIONS

CROSS-REFERENCE TO RELATED APPLICATIONS

This application is a National Phase Application of PCT International Application No. PCT/IL2008/000621, International Filing Date May 6, 2008, which claims the benefit of Provisional Application Ser. No. 60/924,327, filed May 9, 2007 which is incorporated in its entirety by reference herein.

FIELD OF THE INVENTION

The present invention is directed to novel processes for the regioselective preparation of perylenediimides derivatives, specifically mono and dibrominated derivatives.

BACKGROUND OF THE INVENTION

Perylene-diimides (PDIs) are outstanding versatile organic chromophores. They demonstrate exceptional thermal and photochemical stability, strongly absorb visible light, and show high fluorescence quantum yields. PDIs have been utilized as industrial dyes, electronic materials, sensors, photovoltaics, and building blocks for light-harvesting and artificial photosynthetic systems. Importantly, photophysical and redox properties of PDIs can be conveniently modified through substitution in the aromatic core at the positions 1, 6, 7, and 12 (bay region). Substitutions at bay positions and expansion of the PDI core are usually carried out starting from the halogenated derivatives, particularly brominated PDIs. These are almost exclusively synthesized through bromination of perylene dianhydride (PDA) in concentrated $H_2SO_4$ upon heating, followed by imidation with amines. Usually this bromination procedure affords a mixture of di-, tri- and tetrabrominated PDIs. The dibromoperylene diimides contain 1,7 (major) and 1,6 (minor) regioisomers. Recently, purification of 1,7 regioisomer by repetitive recrystallization has been reported. Among the brominated perylene-diimides, 1,7-dibrominated PDIs are the most widely used as starting materials for a broad variety of PDI derivatives.

There is a need in the art to develop synthetic methods for the synthesis of regioselective PDIs compounds, that can provide highly pure products in high yield.

SUMMARY OF THE INVENTION

In one embodiment this invention provides a process for the preparation of dibrominated perylene diimide compound represented by the structures of formula 1,6-3 and 1,7-3;

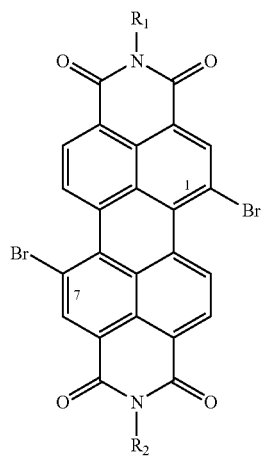

1,7-3

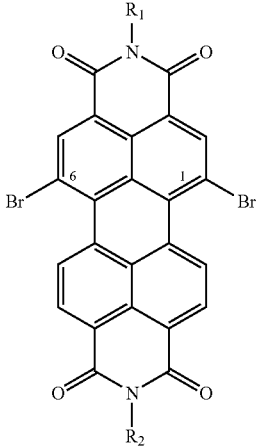

1,6-3 wherein $R_1$ and $R_2$ are the same or different comprising substituted or unsubstituted linear or branched alkyl group, substituted or unsubstituted saturated carbocyclic or heterocyclic ring or aryl;

comprising the steps of a) brominating compound of formula 1

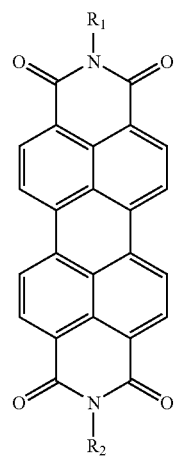

1 wherein $R_1$ and $R_2$ are as defined above;

in the presence of bromine and a chlorinated solvent at reflux for a period of time sufficient to obtain a mixture comprising compounds of formula 1,6-3 and 1,7-3; and b) separating between 1,6-3 and 1,7-3 regioisomer compounds by recrystallizing compound of formula 1,7-3 yielding crystalline pure perylenediimide of formula 1,7-3, thereby separating between said regioisomer compounds.

In one embodiment, this invention provides a process for the preparation of dibrominated perylene-diimide and monobrominated perylene-diimide compounds represented by the structures of formula 2, 1,6-3 and 1,7-3;

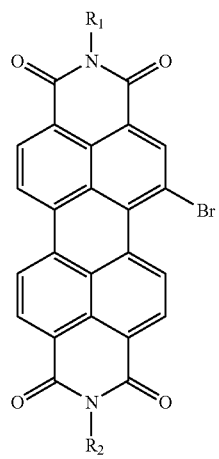

2

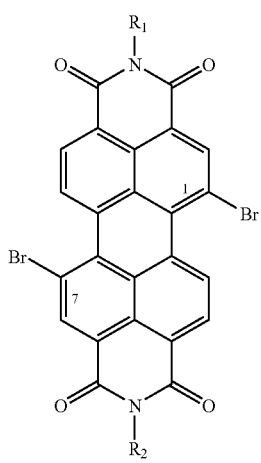

1,7-3

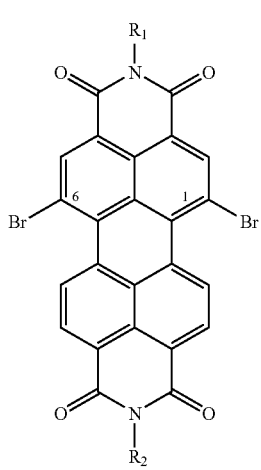

1,6-3 wherein $R_1$ and $R_2$ are the same or different comprising substituted or unsubstituted linear or branched alkyl group, substituted or unsubstituted saturated carbocyclic or heterocyclic ring or aryl;

comprising the steps of
a) brominating compound of formula 1

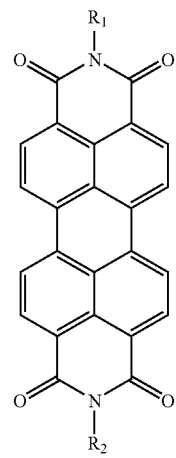

wherein $R_1$ and $R_2$ are as defined above;
in the presence of bromine and a chlorinated solvent at a temperature ranging between about 15-30° C. for a period of time sufficient to obtain a mixture comprising compound of formula 2, 1,6-3 and 1,7-3;
b) isolating compound of formula 2 by chromatography; and
c) separating between 1,6-3 and 1,7-3 regioisomer compounds by recrystallizing compound of formula 1,7-3 yielding crystalline pure perylene-diimide of formula 1,7-3, thereby separating between said two regioisomer compounds.

In one embodiment, this invention provides a perylene-diimide compound represented by the structure of formula 4:

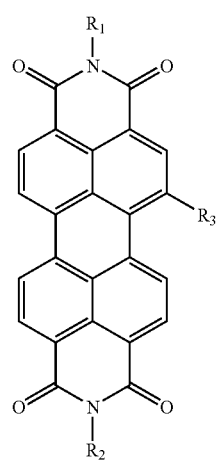

wherein
$R_1$ and $R_2$ are the same or different comprising substituted or unsubstituted linear or branched alkyl group, substituted or unsubstituted saturated carbocyclic or heterocyclic ring or aryl;
$R_3$ is a saturated or unsaturated heterocyclic ring, saturated or unsaturated carbocyclic ring, alkyl, alkylene, alkynyl, acetylene, diphenylacetylene, phenylacetylene, ethynyl-phenyl-2,2';6' 2"-terpyridine, 1,4-diethynylbenzene or Z-perylene;

Z is 1,4 diethynylbenzene, phenyl, acetylene, aryl, cycloalkyl, heterocycle, olefin, azo, amide, C=N, N=C, carbonyl, 1,4 divinylbenzene, piperidine, 5,5'-Diethynyl-2,2'-Bipyridine, dialcohol or dithiol; and optionally a metal or a metal ion is coordinated to said perylene diimide compound forming a metal complex with said compound.

In another embodiment, this invention provides a compound represented by the structure of compound 5:

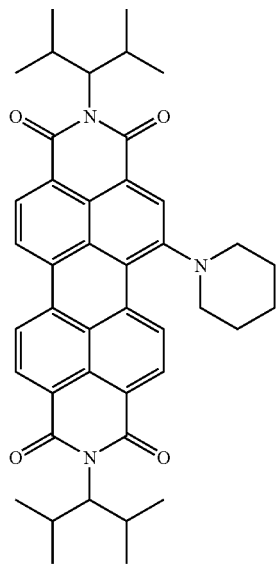

5

In another embodiment, this invention provides a compound represented by the structure of compound 6:

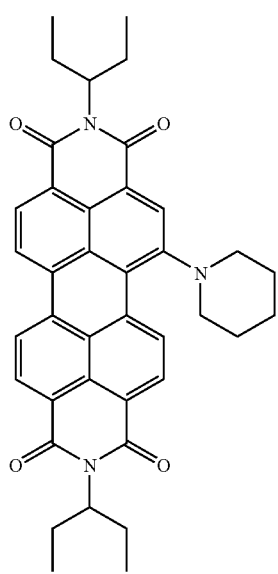

6

In another embodiment, this invention provides a compound represented by the structure of compound 7:

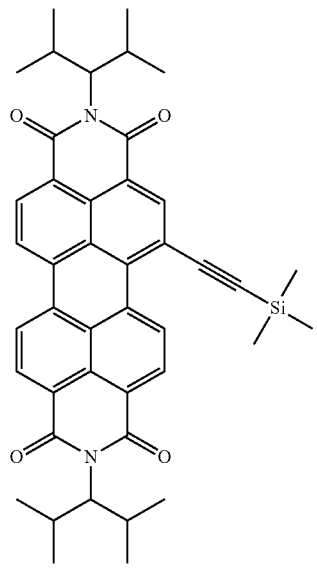

7

In another embodiment, this invention provides a compound represented by the to structure of compound 8:

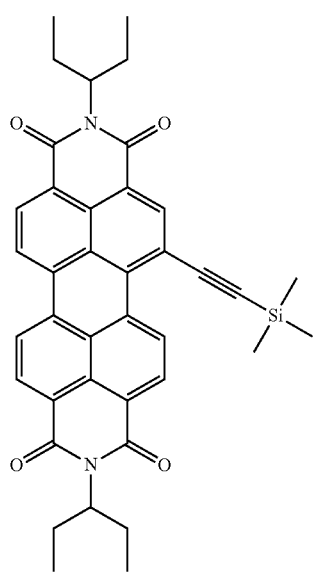

8

In another embodiment, this invention provides a compound represented by the structure of compound 9:

9

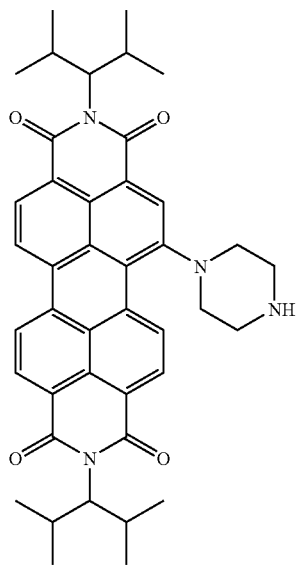

In another embodiment, this invention provides a compound represented by the structure of compound 10:

10

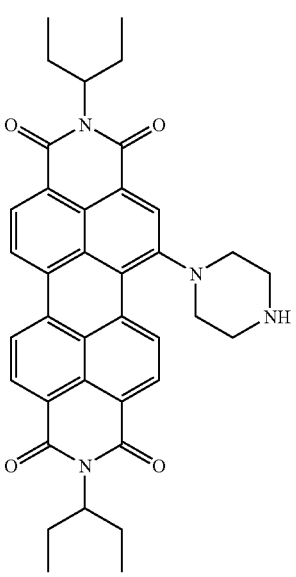

In another embodiment, this invention provides a compound represented by the structure of compound 11:

11

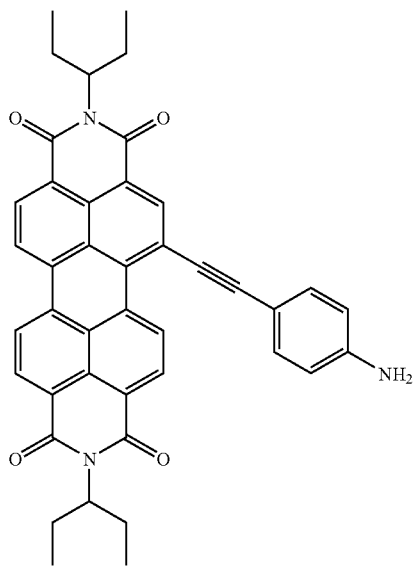

In another embodiment, this invention provides a compound represented by the structure of compound 12:

12

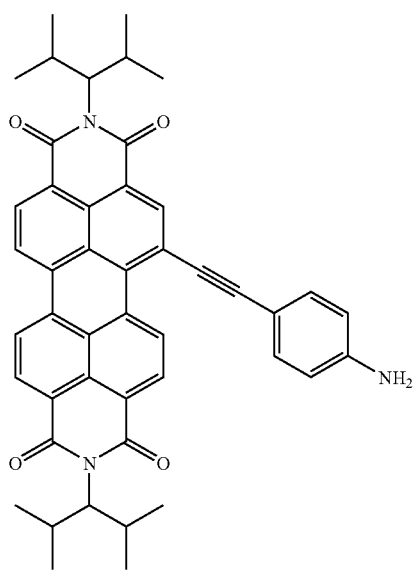

In another embodiment, this invention provides a compound represented by the structure of compound 13:

13

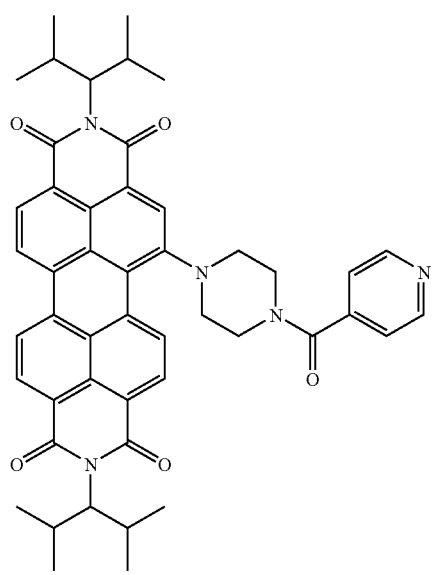

In another embodiment, this invention provides a compound represented by the structure of compound 14:

14

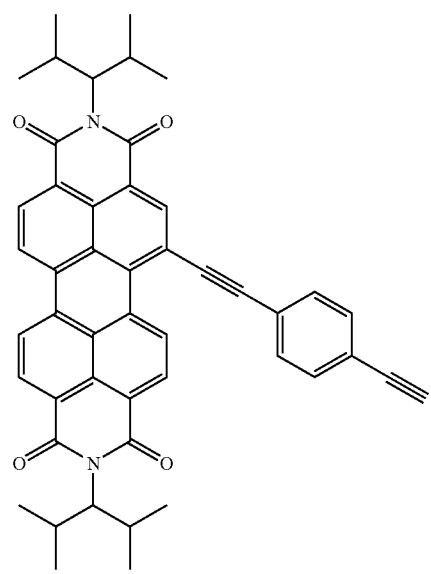

In another embodiment, this invention provides a compound represented by the structure of compound 15:

15

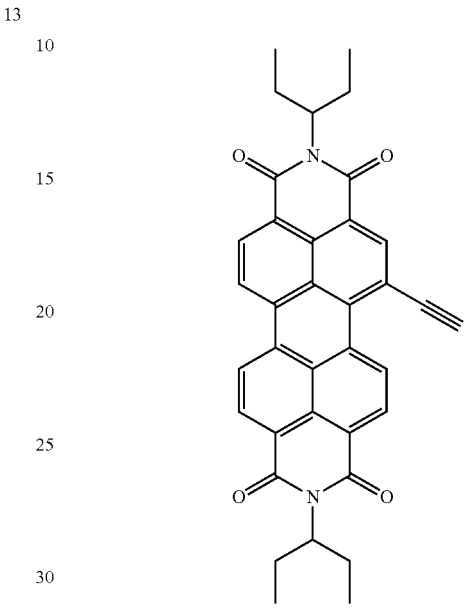

In another embodiment, this invention provides a compound represented by the structure of compound 16:

16

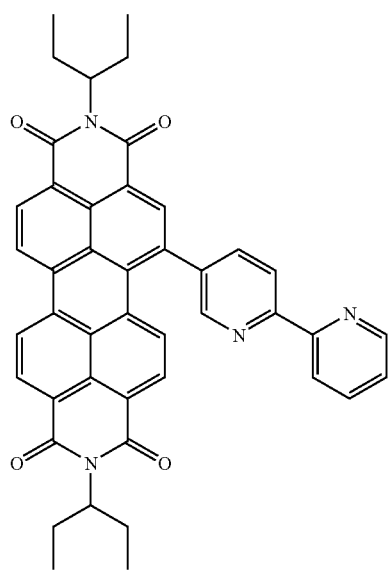

In another embodiment, this invention provides a compound represented by the structure of compound 17:

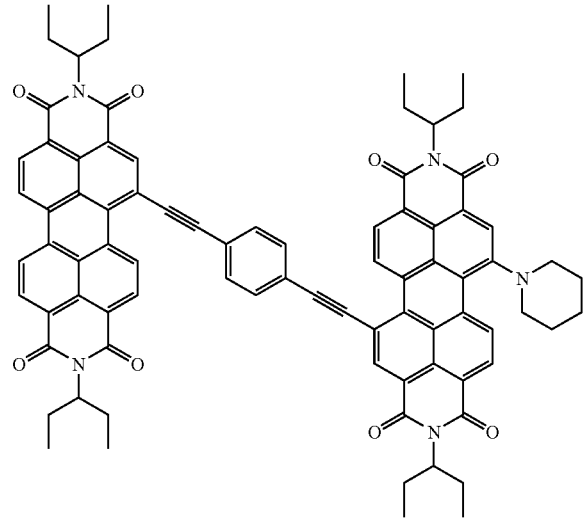

In one embodiment, this invention provides a compound represented by the structure of compound 18:

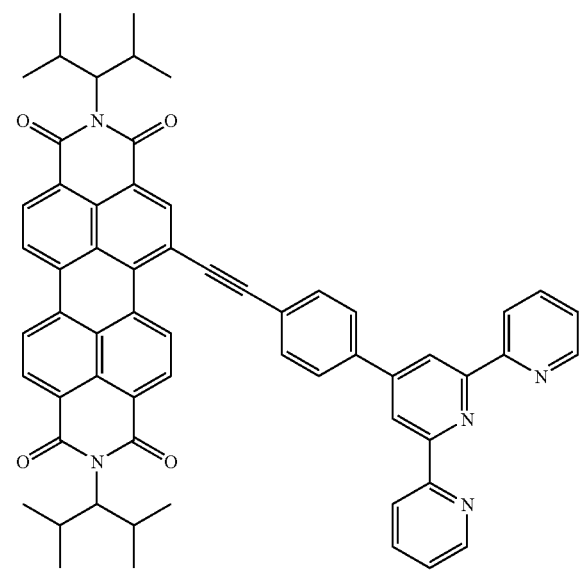

wherein a metal or a metal ion is optionally coordinated with the terpyridine group forming a metal complex.

In one embodiment, this invention provides a compound represented by the structure of compound 19:

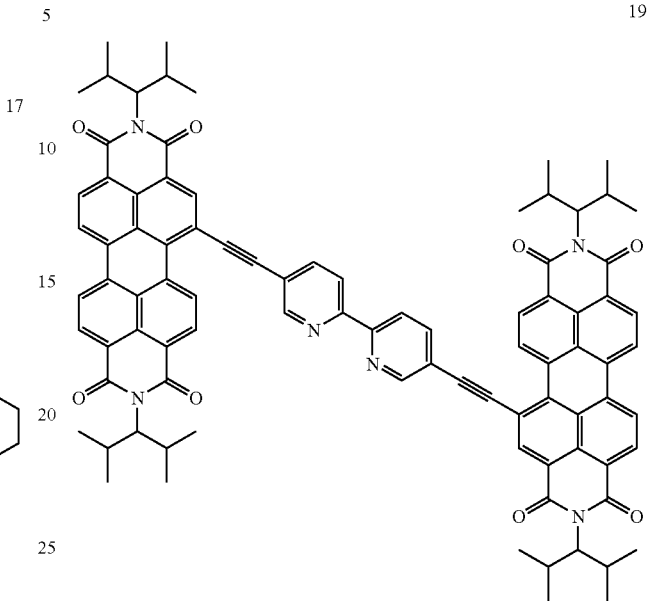

wherein a metal or metal ion is optionally coordinated with the bipyridine group forming a metal complex.

BRIEF DESCRIPTION OF THE DRAWINGS

The present invention will be understood and appreciated more fully from the following detailed description taken in conjunction with the appended drawings in which.

DETAILED DESCRIPTION OF THE PRESENT INVENTION

Figure 1:
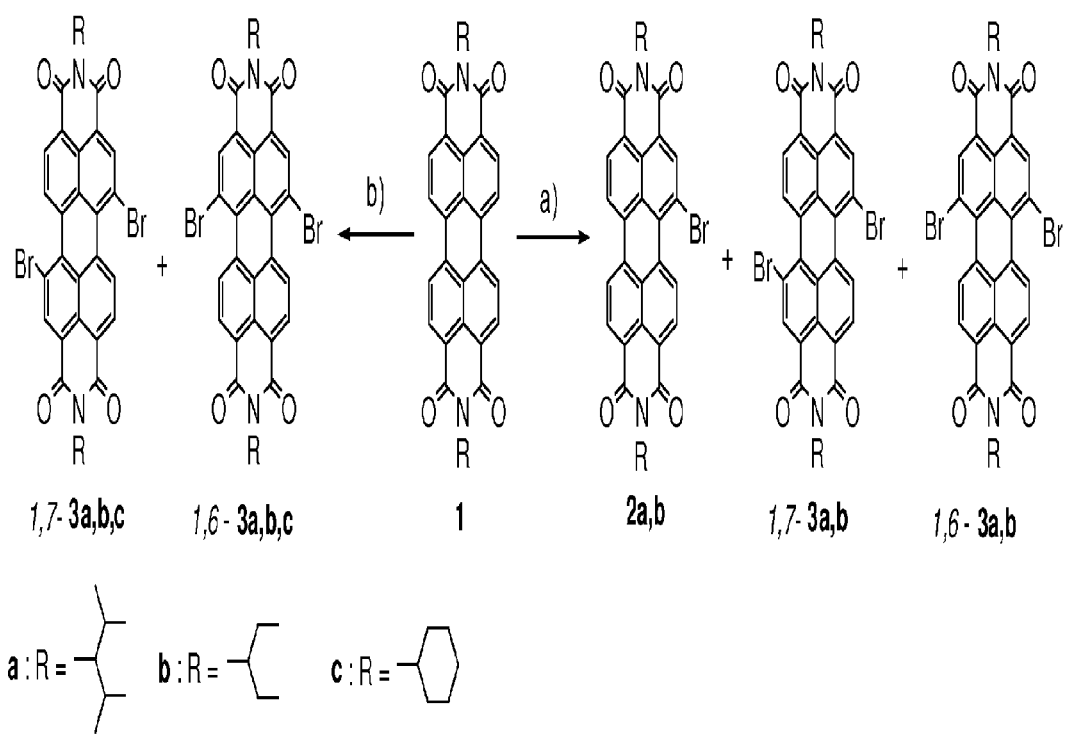
FIG. 1 is a synthetic scheme for the preparation of compounds of formula 2a, 2b, 2c, 3a and 3b providing the reagents and conditions for the different regioisomers: (a) 2a and 3a: $Br_2$, $CH_2Cl_2$, 22-24° C., 2 days, 26% of 2a and 57% of mixture of regioisomers 1,7-3a and 1,6-3a (5:1); 2b and 3b: $Br_2$, $CH_2Cl_2$, 22-24° C., 4 days, 25% of 2b and 50% of mixture of 1,7-3b and 1,6-3b (5:1); (b): 3a: $Br_2$, $CH_2Cl_2$, reflux, 24 hr, 85% of mixture of 1,7-3a and 1,6-3a (3:1); 3b: $Br_2$, $CH_2Cl_2$, reflux, 2 days, 89% of mixture of 1,7-3b and 1,6-3b (3:1); 3c: $Br_2$, $CH_2Cl_2$, reflux, 4 days, 85% of mixture of 1,7-3c and 1,6-3c (3:1).

This invention provides a perylene-diimide bromination methodology that employs mild conditions (organic solvent, room temperature) resulting in facile formation of mono perylene-diimides and dibrominated perylene-diimides. The selectivity of the reaction toward exclusive dibromination can be controlled through variation of the reaction conditions. Computational studies on the imide group rotation and PDI aromatic core provide insight into the inherent dynamics of PDI molecules.

In one embodiment, a dibrominated perylene-diimide compound of this invention refers to 1,7-dibromo-N,N'-Bis (2,4-dimethylpent-3-yl)perylene-3,4:9,10-tetracarboxylic diimide (1,7-3a). In another embodiment, dibrominated perylene-diimide compound of this invention refers to 1,7-dibromo-N,N'-bis(ethylpropyl)perylene-3,4:9,10-tetracarboxylic diimide (1,7-3b). In another embodiment, dibrominated perylene-diimide compound of this invention refers to 1,7-dibromo-N,N'-bis(cyclohexyl)perylene-3,4:9,10-tetracarboxylic diimide (1,7-3c). In another embodiment, dibrominated perylene-diimide compound of this invention refers to 1,6-dibromo-N,N'-Bis(2,4-dimethylpent-3-yl)perylene-3,4:9,10-tetracarboxylic diimide (1,6-3a). In another embodiment, dibrominated perylene-diimide compound of this invention refers to 1,6-dibromo-N,N'-Bis(ethylpropyl) perylene-3,4:9,10-tetracarboxylic diimide (1,6-3b). In another embodiment, dibrominated perylene-diimide compound of this invention refers to 1,6-dibromo-N,N'-Bis(cyclohexyl)perylene-3,4:9,10-tetracarboxylic diimide (1,6-3c)

In another embodiment, monobrominated perylene-diimide compound of this invention refers to 1-bromo N,N'-bis(2, 4-dimethylpent-3-yl) perylene-3,4:9,10-tetracarboxylic diimide (2a). In another embodiment, brominated perylene-diimide compound of this invention refers to 1-bromo N,N'-bis(ethylpropyl)perylene-3,4:9,10-tetracarboxylic diimide (2b).

Some embodiments of a synthetic procedure for some of the PDIs are provided below:

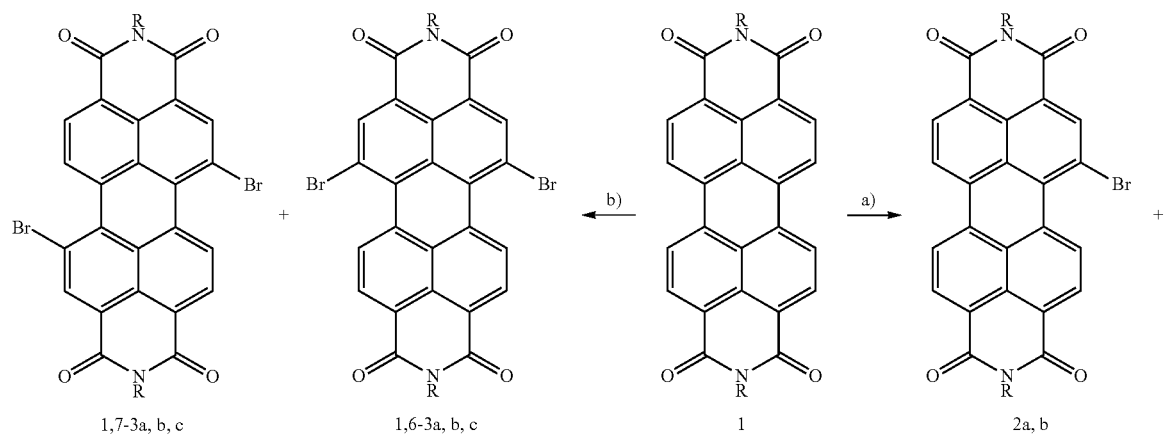

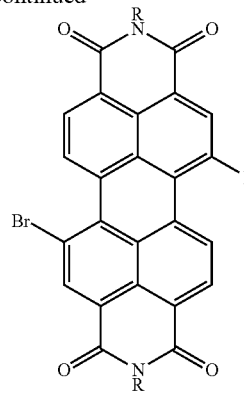

1,7-3a, b

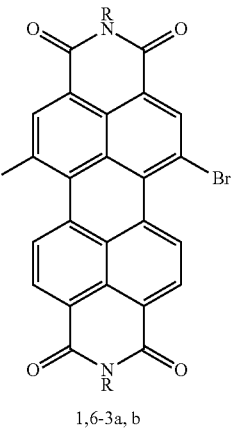

1,6-3a, b

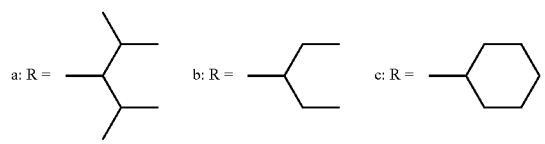

Reagents and Conditions: (a) 2a and 3a: Br$_2$, CH$_2$Cl$_2$, 22-24° C., 2 days, 26% of 2a and 57% of mixture of regioisomers 1,7-3a and 1,6-3a (5:1); 2b and 3b: Br$_2$, CH$_2$Cl$_2$, 22-24° C., 4 days, 25% of 2b and 50% of mixture of 1,7-3b and 1,6-3b (5:1); (b): 3a: Br$_2$, CH$_2$Cl$_2$, reflux, 24 hr, 85% of mixture of 1,7-3a and 1,6-3a (3:1); 3b: Br$_2$, CH$_2$Cl$_2$, reflux, 2 days, 89% of mixture of 1,7-3b and 1,6-3b (3:1); 3c: Br$_2$, CH$_2$Cl$_2$, reflux, 4 days, 85% of mixture of 1,7-3c and 1,6-3c (3:1).

In one embodiment, the solubility of the compounds decreases 1a>1b>1c, reflecting the decrease of the imide substituent bulk and the increase of PDI aggregation propensity, which is controlled by π-π stacking. In another embodiment, bromination of 1a would be highly desirable since it is a starting point for further derivatization, which can lead to novel photonic materials.

In one embodiment, this invention provides, a process for the preparation of dibrominated perylene-diimide compound represented by the structures of formula 1,6-3 and 1,7-3;

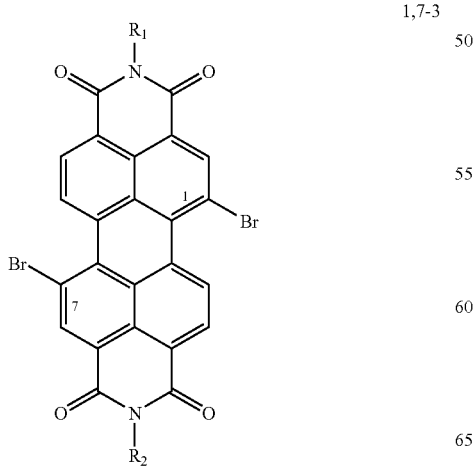

1,7-3

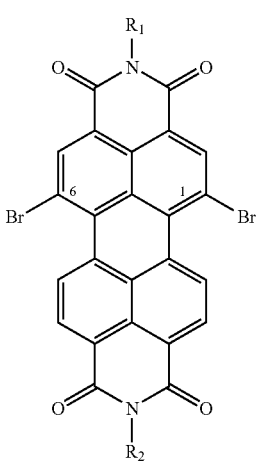

1,6-3 wherein R$_1$ and R$_2$ are the same or different comprising substituted or unsubstituted linear or branched alkyl group, substituted or unsubstituted saturated carbocyclic or heterocyclic ring or aryl;

comprising the steps of a) brominating compound of formula 1

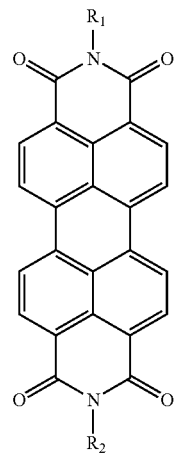

1 wherein $R_1$ and $R_2$ are as defined above;

in the presence of bromine and a chlorinated solvent at reflux for a period of time sufficient to obtain a mixture comprising compounds of formula 1,6-3 and 1,7-3; and b) separating between 1,6-3 and 1,7-3 regioisomer compounds by recrystallizing compound of formula 1,7-3 yielding crystalline pure perylenediimide of formula 1,7-3, thereby separating between said regioisomer compounds.

In one embodiment, this invention provides a process for the preparation of dibrominated perylene-diimide and monobrominated perylene-diimide compounds represented by the structures of formula 2, 1,6-3 and 1,7-3;

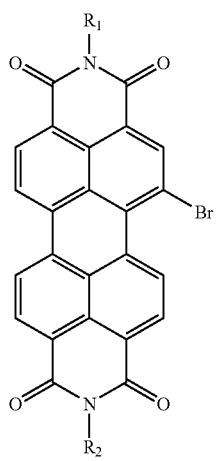

2 wherein $R_1$ and $R_2$ are as defined above;

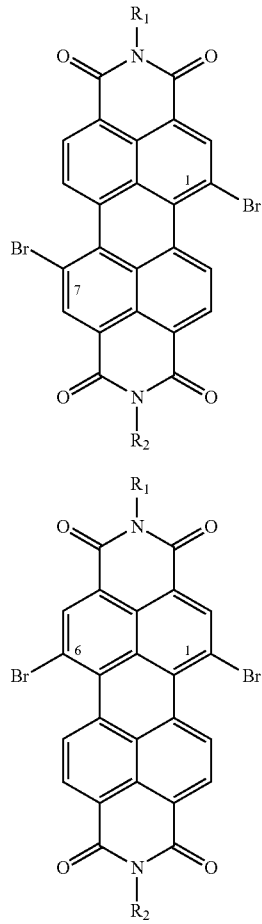

1,7-3

1,6-3 wherein $R_1$ and $R_2$ are the same or different comprising substituted or unsubstituted linear or branched alkyl group, substituted or unsubstituted saturated carbocyclic or heterocyclic ring or aryl;

comprising the steps of a) brominating compound of formula 1

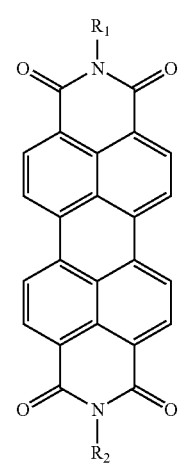

1 wherein $R_1$ and $R_2$ are as defined above;

in the presence of bromine and a chlorinated solvent at a temperature ranging between about 15-30° C. for a period of time sufficient to obtain a mixture comprising compound of formula 2, 1,6-3 and 1,7-3;
b) isolating compound of formula 2 by chromatography; and
c) separating between 1,6-3 and 1,7-3 regioisomer compounds by recrystallizing compound of formula 1,7-3 yielding crystalline pure perylene-diimide of formula 1,7-3, thereby separating between said two regioisomer compounds.

In one embodiment, the processes of this invention comprise a chlorinated solvent. In another embodiment, the chlorinated solvent is dichloromethane (DCM). In another embodiment, the chlorinated solvent is chloroform. In another embodiment, the chlorinated solvent is tetrachloromethane. In another embodiment, the chlorinated solvent is an aliphatic chlorinated solvent.

Some embodiments of the process for the preparation of perylene-diimides compounds of this invention are exemplified herein in Examples 1-15, which serve as guidance for one of skill in the art to practice this invention, which as will be appreciated, may comprise other variations of such processes and compounds, and be within the scope of this invention. According to this aspect, and as exemplified herein, mono-bromination of perylene-diimide compound of formula 1, was accomplished within a period of time of between 1-4 days. In one embodiment, mono-bromination of perylene-diimide compound of formula 1, was accomplished within a period of time of between 24-48 h. In one embodiment, mono-bromination of perylene-diimide compound of formula 1, was accomplished within a period of time of between 24-72 h. In another embodiment, bis-bromination of perylene-diimide compound of formula 1, was accomplished within a period of time of between 1-4 days. In one embodiment, bis-bromination of perylene-diimide compound of formula 1, was accomplished within a period of time of between 24-48 h. In one embodiment, bis-bromination of perylene-diimide compound of formula 1, was accomplished within a period of time of between 24-72 h.

In one embodiment, the processes of this invention provides separation between 1,6-dibromo-perylene-diimide regioisomers and 1,7-dibromo-perylene-diimide regioisomers of this invention. In another embodiment, the separation and/or isolation of 1,7-dibromo-perylene-diimide regioisomers are performed by recrystallization. In another embodiment, the recrystallization is from a mixture of dichloromethane/hexane (v/v, 1:1).

Figure 2:
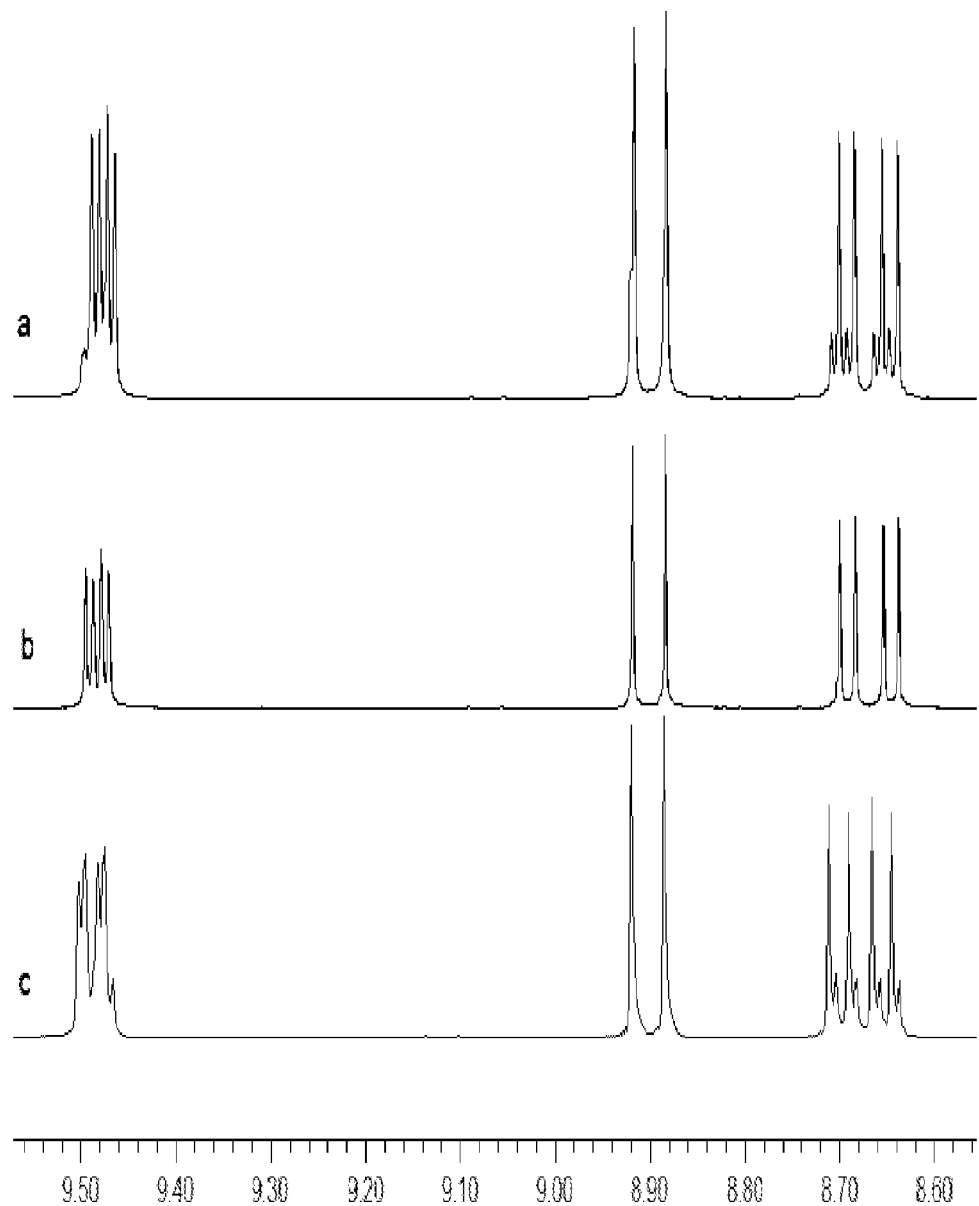
FIG. 2 depicts $^1H$ NMR spectra of a regioisomeric mixture of 1,7-3a and 1,6-3a before recrystallization (FIG. 2A); $^1H$ NMR spectra of 1,7-3a obtained after three repetitive recrystallizations of the regioisomeric mixture, (FIG. 2B); and $^1H$ NMR spectra of the mother liquor obtained in the first recrystallization (1,6-3a is a dominant species) (FIG. 2C).
Figure 3:
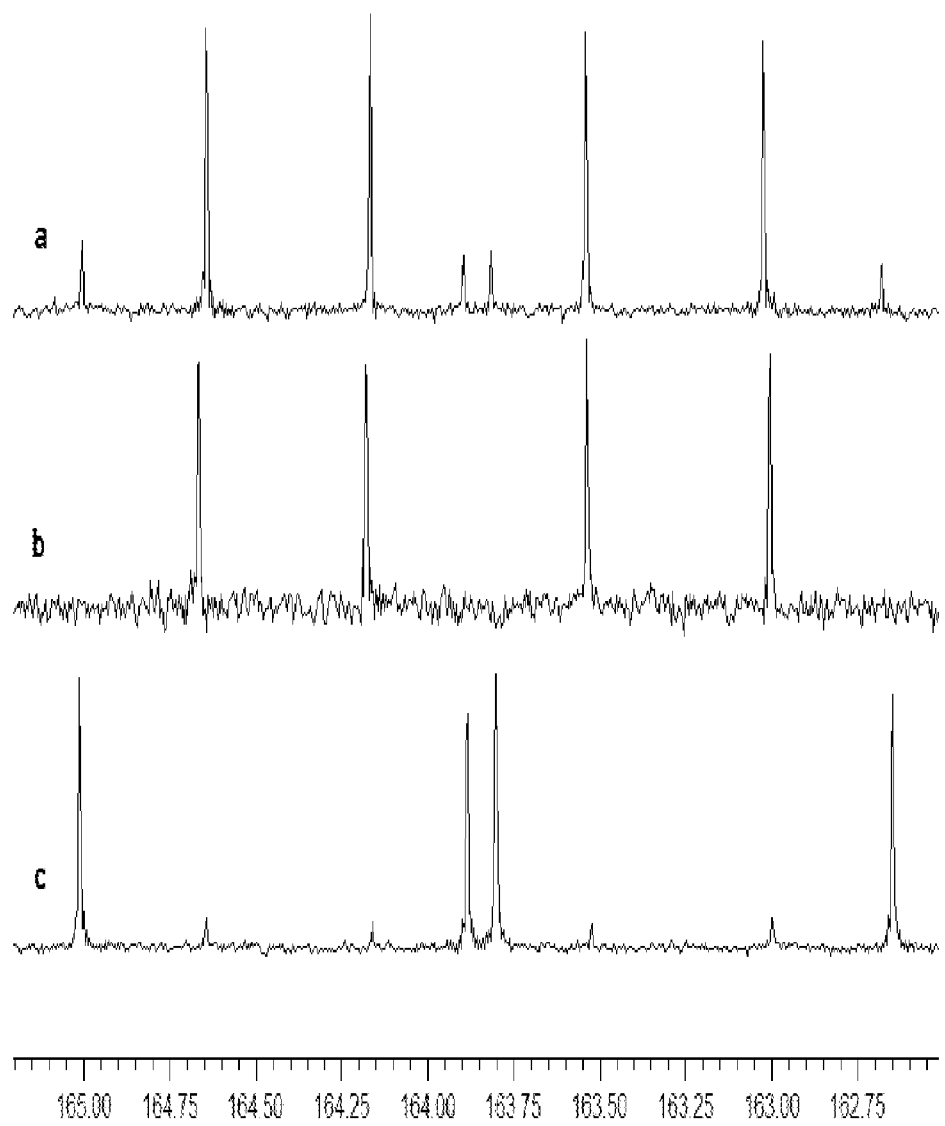
FIG. 3 depicts $^{13}C$ {$^1H$} NMR spectra of carbonyl peaks of regioisomeric mixture of 1,7-3a and 1,6-3a before recrystallization (FIG. 3A); $^{13}C$ {$^1H$} NMR spectra of 1,7-3a obtained after three repetitive recrystallizations of the regioisomeric mixture (FIG. 3B); and $^{13}C$ {$^1H$} NMR spectra of the mother liquor obtained in the first recrystallization (contains mostly 1,6-3a) (FIG. 3C).
Figure 4:
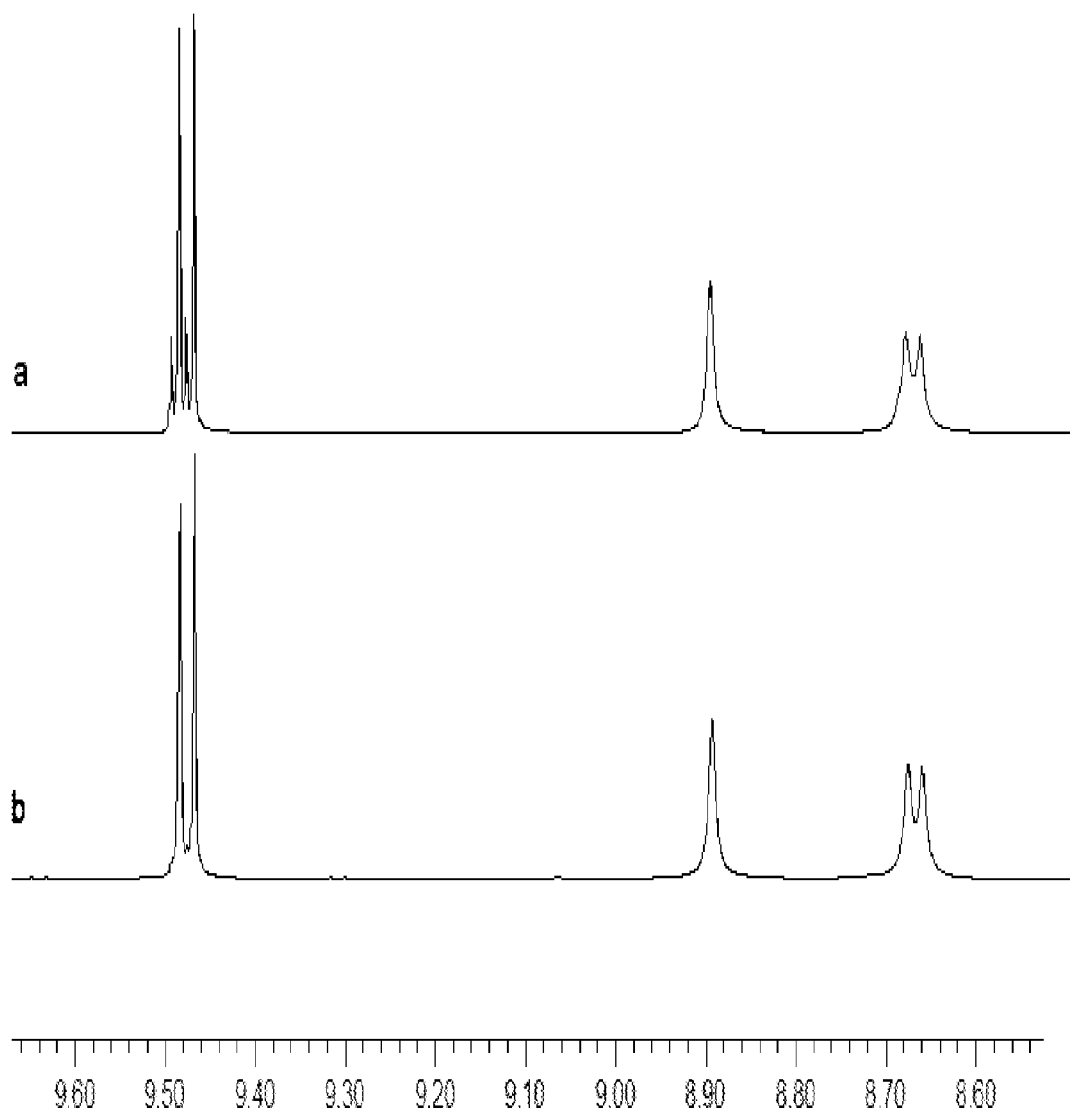
FIG. 4 depicts $^1H$ NMR spectra of a regioisomeric mixture of 1,7-3b and 1,6-3b before recrystallization, (FIG. 4A); and $^1H$ NMR spectra of pure 1,7-3b, obtained after three repetitive recrystallizations of the regioisomeric mixture (FIG. 4B).

In some embodiments, 500 MHz $^1$H NMR spectra of 3 showed the presence of 1,7-3 and 1,6-3 regioisomers (for example in 5:1 ratio respectively, FIG. 2), which could not be separated using column chromatography. The major 1,7-3 regioisomer can be purified by repetitive recrystallization from dichloromethane/hexane mixture (v/v, 1:1). The recrystallization process is monitored by 500 MHz $^1$H NMR spectroscopy (FIG. 2). After successive recrystallizations, the regioisomer 1,7-3 is obtained as indicated by the $^1$H (FIG. 2) and $^{13}$C NMR spectra (FIG. 3). In mother liquor, the isomer 1,6-3 is a major species to (FIGS. 2 and 3).

In one embodiment, the processes of this invention for the preparation of mono-brominated perylene-diimide is conducted at a temperature of between about 15-30° C., or in another embodiment, between about 22-24° C., or in another embodiment, between about 25-30° C., or in another embodiment, between about 18-24° C.

In one embodiment, the processes of this invention for the preparation of bis-brominated perylene-diimide is conducted at a temperature of between about 15-30° C., or in another embodiment, between about 22-24° C., or in another embodiment, between about 25-30° C., or in another embodiment, between about 18-24° C., or in another embodiment, between about 50-60° C., or in another embodiment, at a reflux temperature of the chlorinated solvent.

In one embodiment, high resolution $^1$H and $^{13}$C NMR spectra of compound 1a (starting material in bromination reaction), suggested that two very similar isomers in 1:1 ratio are present. This phenomenon was addressed by computational studies (Example 19), revealing that the isomers are due to restricted rotation (kinetic barrier of ~32 kcal/mol) of the bulky dimethylpentyl group around N—C bond, (FIG. 7) for the structures of the rotational isomers. Restricted rotation of bulky PDI imide substituents (2,5-di-tert-butylphenyls) leading to two isomers has been reported. All dimethylpentyl PDI derivatives described below contain two rotational isomers in 1:1 ratio. Clear observation of the signals for the two isomers in NMR spectra of dimethylpenthyl PDIs was possible only using 500 MHz NMR.

In one embodiment, the facility of the bromination reactions (as exemplified by the reaction times and temperatures) decreases in a row 1a>1b>1c. This trend supports the notion that the reactivity of PDIs depends on their aggregation (which also influences their solubility properties). Notably, while bromination of 1a is very facile at room temperature, compound 1c cannot be brominated at ambient temperatures.

In one embodiment, this invention provides a perylene-diimide compound represented by the structure of formula 4:

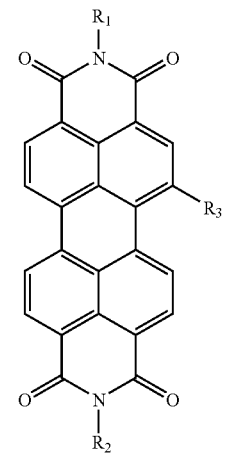

4 wherein
$R_1$ and $R_2$ are the same or different comprising substituted or unsubstituted linear or branched alkyl group, substituted or unsubstituted saturated carbocyclic or heterocyclic ring or aryl;
$R_3$ is saturated or unsaturated heterocyclic ring, saturated or unsaturated carbocyclic ring, alkyl, alkylene, alkynyl, acetylene, diphenylacetylene, ethynyl-phenyl-2,2';6'2"-terpyridine, phenylacetylene, 1,4-diethynylbenzene or Z-perylene;
Z is 1,4 diethynylbenzene, phenyl, acetylene, aryl, cycloalkyl, heterocycle, olefin, azo, amide, C=N, N=C, carbonyl, 1,4 divinylbenzene, piperidine, dialcohol, 5,5'-Diethynyl-2,2'-bipyridine or dithiol; and
optionally a metal or a metal ion is coordinated to said perylene diimide compound forming a metal complex with said compound.

In one embodiment, the perylene-diimide compounds and the compounds used in the process of this invention comprise $R_1$ and $R_2$ substituents. In another embodiment, the $R_1$ and $R_2$ are the same or different comprising substituted or unsubstituted linear or branched alkyl, or substituted or unsubstituted saturated carbocyclic ring. In another embodiment, $R_1$ and $R_2$ comprise substituted or non substituted linear alkyl. In another embodiment, $R_1$ and $R_2$ comprise substituted or unsubstituted branched alkyl. In another embodiment, $R_1$ and $R_2$ comprise substituted or unsubstituted saturated carbocyclic ring. In another embodiment, $R_1$ and $R_2$ comprise substituted or unsubstituted aryl. In another embodiment, $R_1$ and $R_2$ are the same or different comprising dimethylpentyl, tertbutyl, ethylpropyl, linear alkyl ($C_1$-$C_{12}$), cyclohexane, or any combination thereof.

In one embodiment, the perylene-diimide compounds and the compounds used in the process of this invention comprise $R_3$ substituents. In another embodiment, $R_3$ is saturated or unsaturated heterocyclic ring. In another embodiment, $R_3$ is saturated or unsaturated carbocyclic ring. In another embodiment, $R_3$ is alkyl. In another embodiment, $R_3$ is alkylene. In another embodiment, $R_3$ is alkynyl. In another embodiment, $R_3$ acetylene. In another embodiment, $R_3$ is diphenylacetylene. In another embodiment, $R_3$ is phenylacetylene. In another embodiment $R_3$ is piperazine. In another embodiment $R_3$ is pyridine. In another embodiment $R_3$ is bipyridine. In another embodiment, $R_3$ is piperidine. In another embodiment $R_3$ is

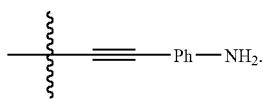

In another embodiment $R_3$ is trimethylsilylethynyl

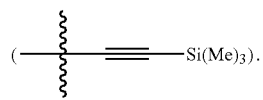

In another embodiment $R_3$ is ethynyl-trimethylsilylbenzene. In another embodiment $R_3$ is -ethynyl-phenyl-2,2';6'2"-terpyridine. In another embodiment, $R_3$ is 1,4-diethynylbenzene. In another embodiment, $R_3$ is Z-perylene wherein Z is 1,4 diethynylbenzene, phenyl, acetylene, aryl, cycloalkyl, heterocycle, olefin, azo, amide, C=N, N=C, carbonyl, 1,4 divinylbenzene, piperidine, dialcohol, 5,5'-Diethynyl-2,2'-bipyridine, or dithiol.

An "alkyl" group refers, in one embodiment, to a saturated aliphatic hydrocarbon, including straight-chain, branched-chain and cyclic alkyl groups. In one embodiment, the alkyl group has 1-12 carbons. In another embodiment, the alkyl group has 1-7 carbons. In another embodiment, the alkyl group has 1-6 carbons. In another embodiment, Examples of alkyl groups are methyl, ethyl, propyl, isobutyl, butyl, pentyl or hexyl. In another embodiment, the alkyl group has 1-4 carbons. The alkyl group may be unsubstituted or substituted by one or more groups selected from halogen, hydroxy, alkoxy, carboxylic acid, aldehyde, carbonyl, amido, cyano, alkylamido, dialkylamido, nitro, amino, alkylamino, dialkylamino, carboxyl, thio and thioalkyl.

An "alkenyl" group refers, in another embodiment, to an unsaturated hydrocarbon, including straight chain, branched chain and cyclic groups having one or more double bonds. The alkenyl group may have one double bond, two double bonds, three double bonds, etc. In another embodiment, the alkenyl group has 2-12 carbons. In another embodiment, the alkenyl group has 2-6 carbons. In another embodiment, the alkenyl group has 2-4 carbons. In another embodiment the alkenyl group is ethenyl (—CH=CH$_2$) Examples of alkenyl groups are ethenyl, propenyl, butenyl, cyclohexenyl, etc. The alkenyl group may be unsubstituted or substituted by a halogen, hydroxy, alkoxy carbonyl, amido, alkylamido, dialkylamido, nitro, cyano, amino, alkylamino, dialkylamino, carboxyl, thio and/or thioalkyl.

An "alkynyl" group refers, in another embodiment, to an unsaturated hydrocarbon, including straight chain, branched chain and cyclic groups having one or more triple bonds. The alkynyl group may have one triple bond, two triple bonds, three triple bonds, etc. In another embodiment, the alkynyl group has 2-12 carbons. In another embodiment, the alkynyl group has 2-6 carbons. In another embodiment, the alkynyl group has 2-4 carbons. In another embodiment the alkynyl group is ethynyl. Examples of alkenyl groups are ethynyl, propynyl, butynyl, cyclohexynyl, etc. The alkynyl group may be unsubstituted or substituted by a halogen, hydroxy, alkoxy carbonyl, cyano, amido, alkylamido, dialkylamido, nitro, amino, alkylamino, dialkylamino, carboxyl, thio and/or thioalkyl.

In one embodiment, the term "halogen refers to in one embodiment to F, in another embodiment to Cl, in another embodiment to Br, in another embodiment to I.

A "carbocyclic ring" group refers, in one embodiment, to a saturated or non saturated hydrocarbon ring. In one embodiment, the carbocyclic ring group has 4-12 carbons. In another embodiment, the carbocyclic ring group has 4-8 carbons. In another embodiment, the carbocyclic ring comprise of 2-3 fused rings. In another embodiment, Examples of a carbocyclic ring are cyclohexane, cyclopentane, phenyl or 1-cyclopentene. The carbocyclic ring may be substituted by one or more groups selected from halogen, hydroxy, alkoxy, carboxylic acid, aldehyde, carbonyl, amido, cyano, alkylamido, dialkylamido, nitro, amino, alkylamino, dialkylamino, carboxyl, thio and thioalkyl.

A "heterocycle" group refers, in one embodiment, to a ring structure comprising in addition to carbon atoms, sulfur, oxygen, nitrogen or any combination thereof, as part of the ring. In another embodiment the heterocycle is a 3-12 membered ring. In another embodiment the heterocycle is a 6 membered ring. In another embodiment the heterocycle is a 5-7 membered ring. In another embodiment the heterocycle is a 4-8 membered ring. In another embodiment, the hetrocycle is terpyridine, piperazine, piperidine, pyridine, thiophen, furane, pyrrole, pyrrolidine, bipyridine or pyrazine. In another embodiment, the heterocycle group may be unsubstituted or substituted by a halogen, haloalkyl, hydroxyl, alkoxy, carbonyl, amido, alkylamido, dialkylamido, cyano, nitro, $CO_2H$, amino, alkylamino, dialkylamino, carboxyl, thio and/or thioalkyl. In another embodiment, the heterocycle ring may be fused to another saturated or unsaturated cycloalkyl or heterocyclic 3-8 membered ring. In another embodiment, the heterocyclic ring is a saturated ring. In another embodiment, the heterocyclic ring is an unsaturated ring.

In one embodiment, this invention provides a compound represented by the structure of compound 5:

5

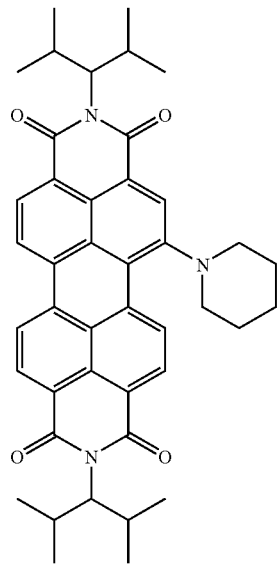

In one embodiment, this invention provides a compound represented by the structure of compound 6:

6

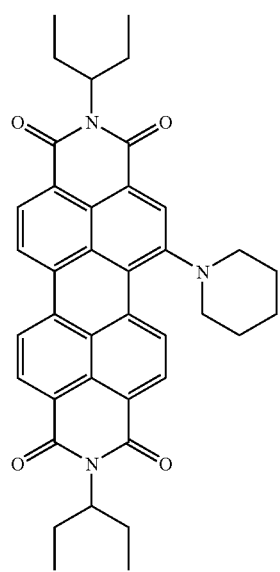

In one embodiment, this invention provides a compound represented by the structure of compound 7:

7

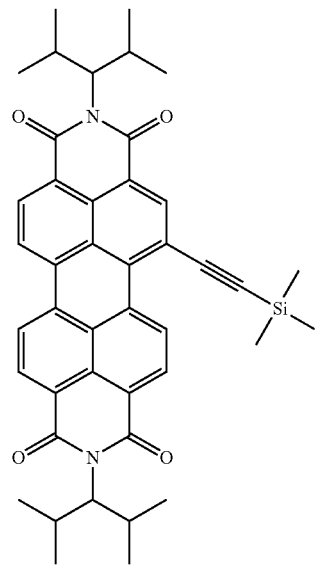

In one embodiment, this invention provides a compound represented by the structure of compound 8:

8

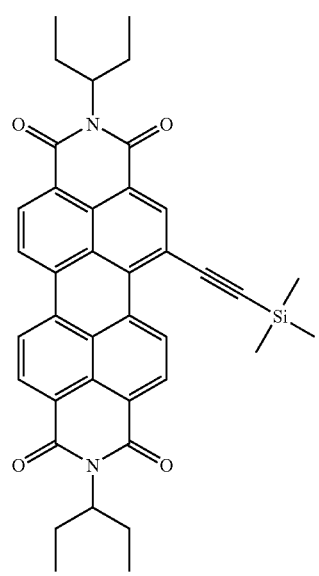

In one embodiment, this invention provides a compound represented by the structure of compound 9:

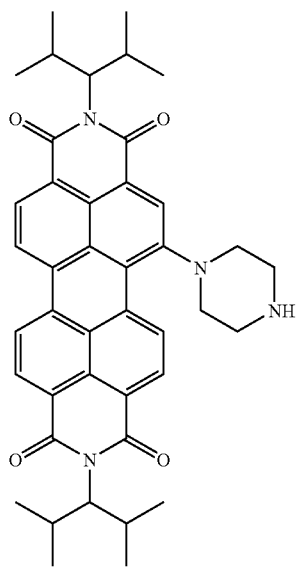

In one embodiment, this invention provides a compound represented by the structure of compound 10:

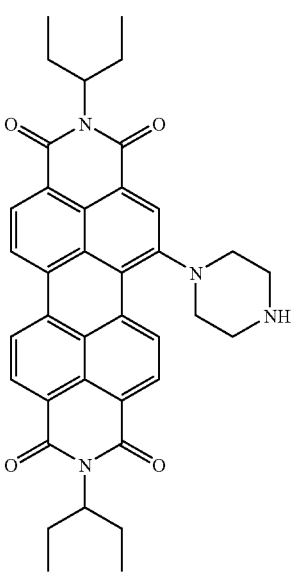

In one embodiment, this invention provides a compound represented by the structure of compound 11:

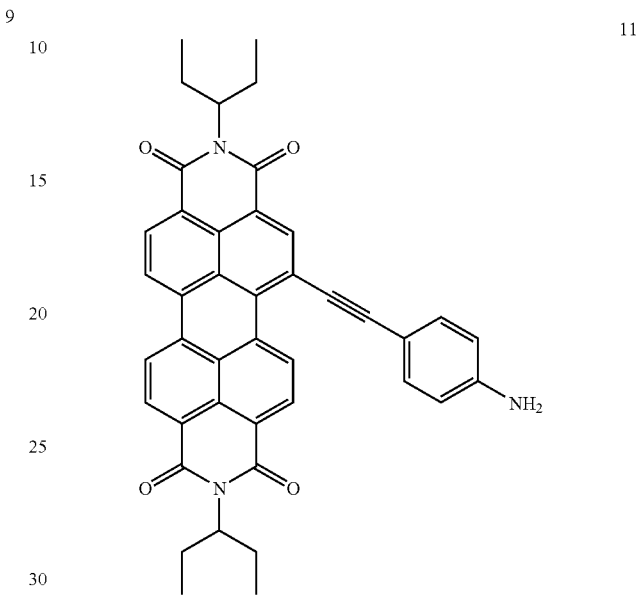

In one embodiment, this invention provides a compound represented by the structure of compound 12:

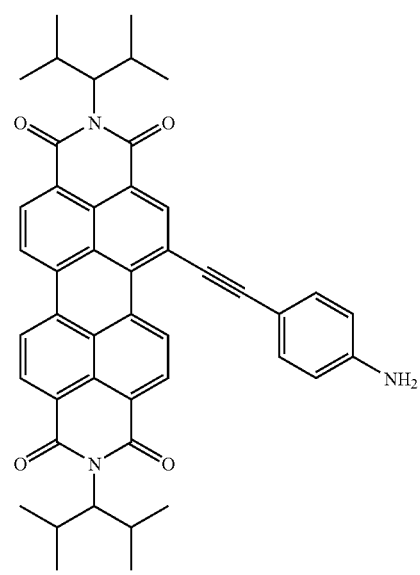

In one embodiment, this invention provides a compound represented by the structure of compound 13:

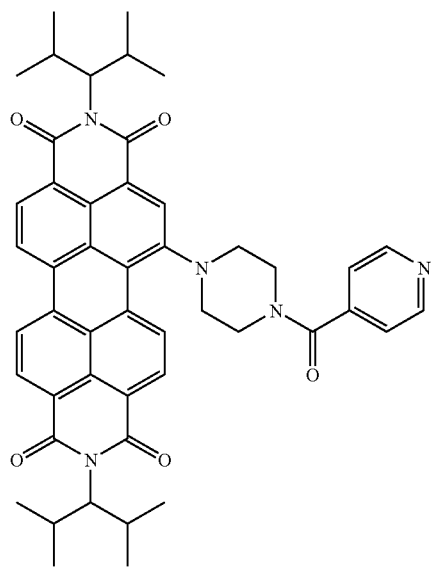

13

In one embodiment, this invention provides a compound represented by the structure of compound 15:

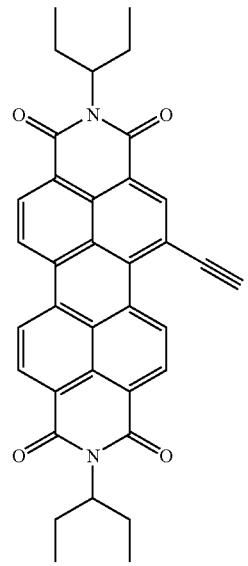

15

In one embodiment, this invention provides a compound represented by the structure of compound 14:

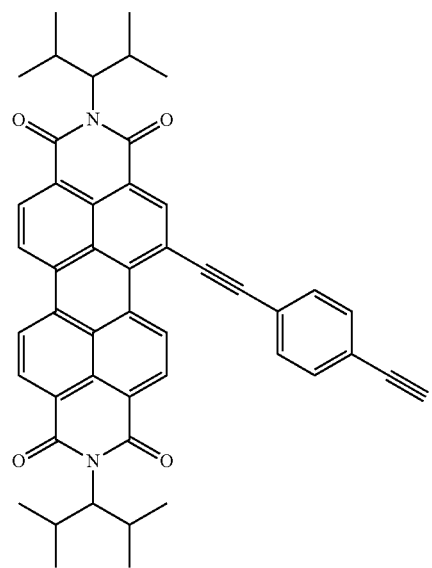

14

In one embodiment, this invention provides a compound represented by the structure of compound 16:

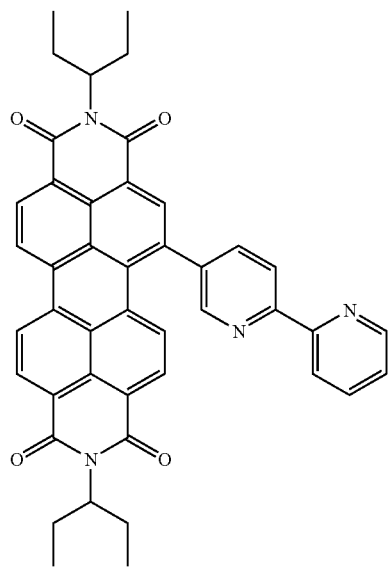

16

In one embodiment, this invention provides a compound represented by the structure of compound 17:

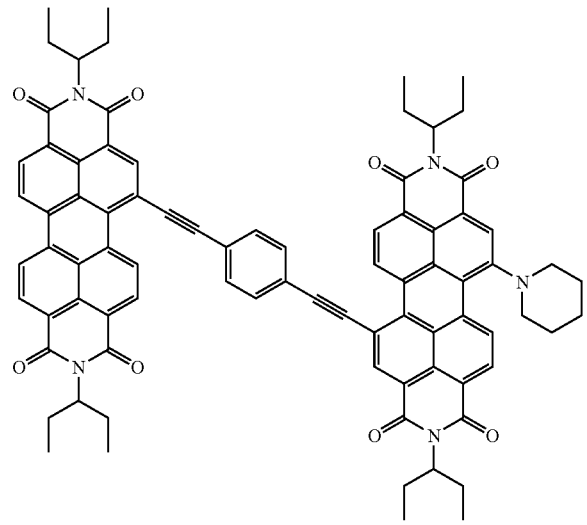

17

In one embodiment, this invention provides a compound represented by the structure of compound 19:

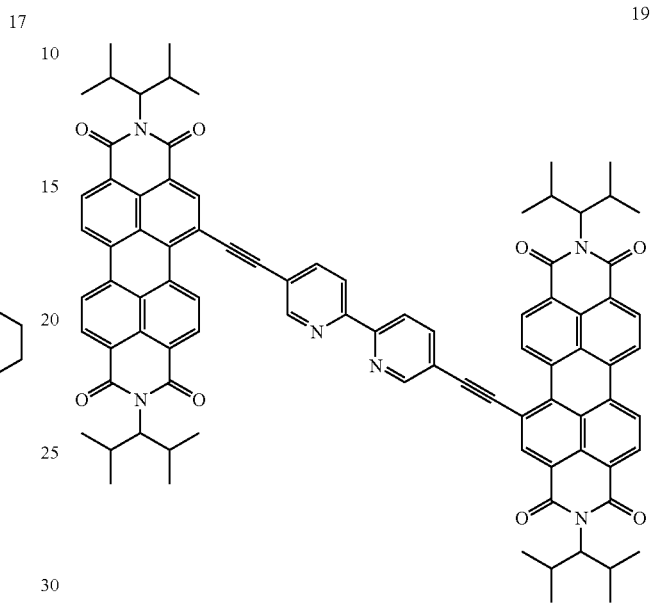

19

In one embodiment, this invention provides a compound represented by the structure of compound 18:

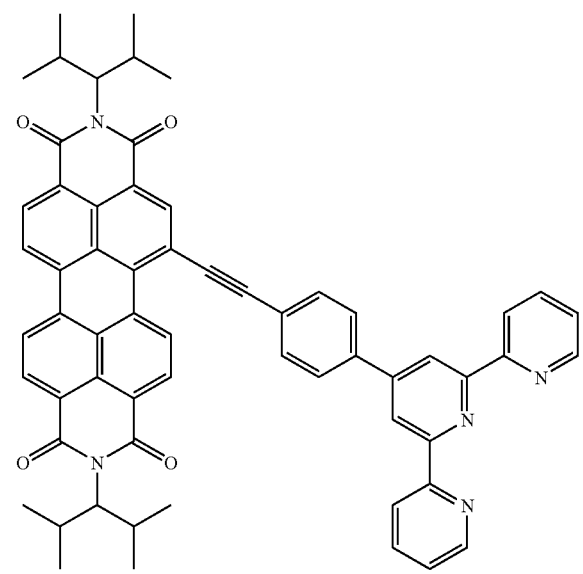

18 wherein a metal or metal ion is optionally coordinated with the terpyridine group forming a metal complex.

wherein a metal or metal ion is optionally coordinated with the bipyridine group forming a metal complex.

In another embodiment, a metal is optionally coordinated to the compounds of this invention via a chelating group. In another embodiment, Z, $R_1$, $R_2$ and $R_3$ comprise independently a chelating group, wherein the chelating group is attached directly or indirectly to the perylene or imide. In another embodiment, the chelating group is attached via an ethenyl to bridge, phenyl bridge, or any combination thereof. In another embodiment, the chelating group forms a complex with a metal or metal ion. In another embodiment, the metal or metal ion comprises Pd, Pt, Fe, Cu, Ag, Rh, Ir, Ru or Os. In another embodiment the chelating agent comprises a diamine, a dicarboxylic acid, a pyridine, a bipyridine, a terpyridine, a diazo, a mercapto, a acetylacetone, a benzoylacetone, a salysilic acid, a carboxylic acid, an ethylene diamine tetraacetic acid (EDTA) moeity, or any combination thereof. In another embodiment, compounds (18) and (19) are exemplified compounds which possess a chelating group.

In one embodiment, the preparation of monobrominated PDIs (2a,b) is disclosed hereinabove and exemplified in Examples 1 and 2. Compounds of formula 2a and 2b they are used, in some embodiments for further functionalization at the bay position to give novel unsymmetrical derivatives. Some embodiments of a synthetic procedure for some of the PDIs are provided below:

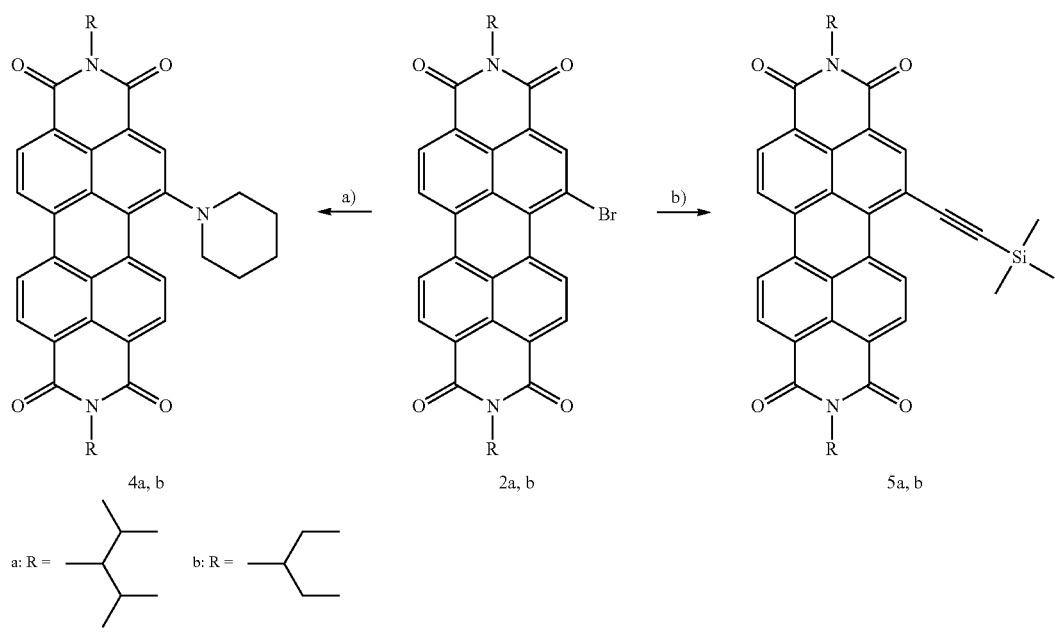

Reagents and Conditions: (a) Piperidine, 60° C., $N_2$, 5 h, 96% of 4a and 96% of 4b;
(b) $Pd(PPh_3)_4$ (10 mol %), CuI (5 mol %), trimethyl silyl acetylene, diisopropyl amine, rt, 96% of 5a and 97% of 5b.

In one embodiment, The nucleophilic substitution of mono bromoperylene diimide (2a,b) with piperidine afforded the corresponding monopiperidinyl-diimides 5 and 6. Sonogashira cross-coupling afforded ethynyl derivatives 7 and 8 (Examples 4-7).

In one embodiment, the compounds of this invention are incorporated in electroluminescent devices such as thin-film. In another embodiment, the compounds of this invention modify the light emitted in electroluminescent devices. In another embodiment, the compounds of this invention are incorporated in the electroluminescent layer or in the electron transmitting layer. In another embodiment, the light is emitted in the electroluminescent material layer in response to the injection and combination of holes in the layer. If a fluorescent material is added to the electroluminescent the color of the emitted light can be varied. In theory, if an electroluminescent host material and a fluorescent material could be found for blending which have exactly the same affinity for hole-electron recombination each material should emit light upon injection of holes and electrons in the luminescent zone. Choosing fluorescent materials capable of providing favored sites for light emission necessarily involves relating the properties of the fluorescent material to those of the host material. The host material can be viewed as a collector for injected holes and electrons with the fluorescent material providing the molecular sites for light emission.

The following examples are presented in order to more fully illustrate the preferred embodiments of the invention. They should in no way be construed, however, as limiting the broad scope of the invention.

EXAMPLES

Materials and Methods

General Methods. Solvents and reagents were obtained from commercial sources and used as received. NMR spectra were recorded at room temperature on 500 MHz NMR spectrometer unless otherwise specified. $CDCl_3$ was used as an NMR solvent. The chemical shifts ($\delta$) are reported in parts per million (ppm) from tetramethylsilane (TMS, 0.00 ppm). Proton spectra recorded in $CDCl_3$ were referenced to TMS. Carbon spectra recorded in $CDCl_3$ were referenced to the peak of $CDCl_3$ (77.0 ppm).

The solvents for spectroscopic studies were of spectroscopic grade and used as received. UV/vis spectra were measured on a Cary spectrometer. Steady-state fluorescence spectra were measured on a Cary Eclipse instrument and fluorescence quantum yields were determined using N,N'-Bis (2,4-dimethylpent-3-yl)perylene-3, 4:9,10-tetracarboxylic-diimide ($\Phi=1$) as reference for compounds 2a, 2b, 3a, 3b, 7 and 8 and N,N'-Dicyclohexyl-1,7-dipiperidinylperylene-3,4: 9,10-tetracarboxylic diimide ($\Phi=0.2$) as reference for compounds 5 and 6.

Electrochemical measurements were performed using a CHI electrochemical workstation. Methylene chloride containing 0.1M tetra-n-butylammonium hexafluorophosphate ($TBAPF_6$) was used as a solvent. Ferrocene/ferrocenium redox couple ($Fc/Fc^+$, 0.475 V vs SCE in $CH_2Cl_2$) was used as an internal reference for all measurements. All electrochemical measurements were performed under dry nitrogen atmosphere. Electrospray Ionization (ESI) Mass-Spectrometry was performed using Micromass Platform instrument. Melting points for all compounds exceeded 300° C.

Example 1

Synthesis of 1-bromo N,N'-Bis(2,4-dimethylpent-3-yl)perylene-3,4:9,10-tetracarboxylic diimide (2a) and 1,7-dibromo-N,N'-Bis(2,4-dimethylpent-3-yl) perylene-3,4:9,10-tetracarboxylic diimide (1,7-3a)

Bromination of N,N'-Bis(2,4-dimethylpent-3-yl)perylene-3,4:9,10-tetracarboxylic diimide (1a). A mixture of 1a (1 g, 1.7 mmol) and bromine (18.66 g, 0.116 mol) in 60 ml of dichloromethane was stirred at 22-24° C. in a closed round bottom flask for 2 days. The excess of bromine was removed by air bubbling and the solvent was removed under vacuum. The crude product was purified by silica gel column chromatography with chloroform as an eluent. The first band was collected to afford dibromo perylene diimide (mixture of 1,7-3a and 1,6-3a in 5:1 ratio) as an orange solid (330 mg, 26%). The second band afforded 1-bromo N,N'-Bis(2,4-dimethyl pent-3-yl)perylene diimide 2a (650 mg, 57%) as an orange solid. The third to band gave the unreacted perylene diimide 1(150 mg, 15%). The regioisomers, 1,7-3a and 1,6-3a, could not be separated by column chromatography.

Regioisomerically pure 1,7-dibromo perylene diimide (1,7-3a) was obtained by repetitive crystallization. The mixture (330 mg) of 1,7-3a and 1,6-3a (5:1) was crystallized from 50 ml of $CH_2Cl_2$:Hexane (v/v, 1:1) mixture at room temperature for 5 days. The crystallization was repeated at the same conditions for two more times to yield 180 mg (55%) of pure 1,7-3a as an orange solid.

1-bromo N,N'-Bis(2,4-dimethylpent-3-yl)perylene-3,4:9,10-tetracarboxylic diimide (2a) $^1$H NMR: δ 9.8 (m, 2H), 8.96 (s, 1H), 8.93 (s, 1H), 8.6-8.75 (m, 10H), 4.75 (m, 4H), 2.72 (m, 8H), 1.13 (d, 12H, J=6.5 Hz), 1.12 (d, 12H, J=7.0 Hz), 0.95 (d, 12H, J=7.0 Hz), 0.94 (d, 12H, J=6.5 Hz). $^{13}$C {$^1$H} NMR: δ 165.26, 164.94, 164.89, 164.13, 164.09, 163.81, 163.77, 162.93, 139.58, 138.94, 133.97, 133.94, 133.91, 133.88, 133.63, 133.60, 133.58, 133.57, 133.53, 131.61, 131.09, 130.90, 130.38, 128.92, 128.91, 128.72, 128.71, 128.11, 128.09, 127.04, 124.03, 124.02, 123.86, 123.84, 123.78, 123.75, 123.56, 123.54, 123.41, 123.39, 123.25, 123.23, 123.01, 123.00, 122.98, 122.96, 122.94, 122.66, 122.64, 120.97, 120.95, 120.92, 65.41, 65.35, 65.20, 65.19, 29.11, 29.10, 29.06, 29.01, 21.80, 21.72, 20.57, 20.51, 20.50. MS 664.50 [$M^+$] (calcd 664.19). UV/vis ($CHCl_3$): $\lambda_{max}$/nm ($\epsilon/M^{-1}$ $cm^{-1}$)=524 (74 669), 488 (48 630), 458 (18 465). Fluorescence ($CHCl_3$): $\lambda_{max}$=538 nm, fluorescence quantum yield $\Phi_f$=0.92. Anal. Calcd. for $C_{38}H_{37}BrN_2O_4$: C, 68.57; H, 5.60; N, 4.21. Found: C, 68.43; H, 5.61; N, 4.33.

1,7-dibromo-N,N'-Bis(2,4-dimethylpent-3-yl)perylene-3,4:9,10-tetracarboxylic diimide (1,7-3a). $^1$H NMR: δ 9.52 (d, 1H, J=8.0 Hz), 9.50 (d, 1H, J=8.0 Hz), 8.95 (s, 1H), 8.92 (s, 1H), 8.73 (d, 1H, J=8.0 Hz), 8.68 (d, 1H, J=8.0 Hz), 4.75 (two triplets merged t, 2H, J=8.5 Hz), 2.72 (m, 4H), 1.12 (d, 12H, J=7.0 Hz), 0.94 (d, 12H, J=7.0 Hz). $^{13}$C {$^1$H} NMR: δ 164.66, 164.17, 163.53, 163.00, 138.53, 137.90, 132.90, 132.88, 132.84, 132.77, 132.71, 130.57, 129.86, 129.25, 128.45, 127.14, 123.63, 123.24, 123.22, 123.02, 123.00, 122.64, 122.62, 120.76, 65.44, 65.36, 29.05, 29.02, 21.72, 20.49. MS 742.38 [$M^+$] (calcd 742.10). UV/vis ($CHCl_3$): $\lambda_{max}$/nm ($\epsilon/M^{-1}$ $cm^{-1}$)=526 (49 825), 490 (33 702), 463 (13 458). Fluorescence ($CHCl_3$): $\lambda_{max}$=545 nm, fluorescence quantum yield $\Phi_f$=0.82. Anal. Calcd. for $C_{38}H_{36}Br_2N_2O_4$: C, 61.30; H, 4.87; N, 3.76. Found: C, 61.35; H, 4.89; N, 3.80.

Example 2

Synthesis of 1-bromo N,N'-Bis(ethylpropyl) perylene-3,4:9,10-tetracarboxylic diimide (2b) and 1,7-dibromo-N,N'-Bis(ethylpropyl)perylene-3,4:9,10-tetracarboxylic diimide (1,7-3b)

Bromination of N,N'-Bis(ethylpropyl)perylene-3,4:9,10-tetra carboxylic diimide (1b). A mixture of 1b (2 g, 3.77 mmol) and bromine (31.1 g, 0.194 mol) in 100 ml of dichloromethane was stirred at 22-24° C. in a closed round bottom flask for 4 days. The excess of bromine was removed by air bubbling and the solvent was removed under vacuum. The crude product was purified by silica gel column chromatography with chloroform as an eluent. The first band was collected to afford dibromo perylene diimide (red solid, 650 mg, 25%) as a mixture of regioisomers (1,7-3b:1,6-3b=5:1). The second band yielded 1-bromo N,N'-Bis(ethyl propyl) perylene diimide 2b (1.15 g, 50%) as a red solid. The third band gave the unreacted perylene diimide (500 mg, 25%). The regioisomeric dibromoperylene diimides 1,7-3b and 1,6-3b could not be separated by column chromatography.

Regioisomerically pure 1,7-dibromo perylene diimide (1,7-3b) was obtained by repetitive crystallization. The mixture (200 mg) of 1,7-3b and 1,6-3b (5:1) was crystallized from 50 ml of $CH_2Cl_2$:Hexane (v/v, 1:1) mixture at room temperature for 5 days. The crystallization was repeated at the same conditions for two more times to yield 80 mg (40%) of pure 1,7-3b as a red solid.

1-bromo N,N'-Bis(ethylpropyl)perylene-3,4:9,10-tetracarboxylic diimide (2b). $^1$H NMR: δ 9.78 (d, 1H, J=8.5 Hz), 8.92 (s, 1H), 8.69 (m, 3H), 8.62 (d, 1H, J=8.5 Hz), 8.61 (d, 1H, J=8.0 Hz), 5.07 (m, 2H), 2.27 (m, 4H), 1.95 (m, 4H), 0.94 (t, 6H, J=7.5 Hz), 0.93 (t, 6H, J=7.5 Hz). $^{13}$C {$^1$H} NMR (323K): δ 164.09, 163.79, 163.72, 162.89, 139.04, 133.92, 133.55, 133.48, 130.91, 130.38, 129.04, 128.84, 128.22, 128.03, 127.13, 124.03, 123.87, 123.51, 123.20, 122.75, 120.78, 58.08, 57.88, 25.04, 24.99, 11.08, 11.06. MS 608.36 [$M^+$] (calcd 608.13). UV/vis ($CHCl_3$): $\lambda_{max}$/nm ($\epsilon/M^{-1}$ $cm^{-1}$)=524 (61 578), 488 (40 027), 458 (15 254). Fluorescence ($CHCl_3$): $\lambda_{max}$=537 nm, fluorescence quantum yield $\Phi_f$=0.84. Anal. Calcd. for $C_{34}H_{29}BrN_2O_4$: C, 67.00; H, 4.80; N, 4.60. Found: C, 66.81; H, 4.90; N, 4.53.

1,7-dibromo-N,N'-Bis(ethylpropyl)perylene-3,4:9,10-tetracarboxylic diimide (1,7-3b). $^1$H NMR: δ 9.50 (d, 2H, J=8.0 Hz), 8.9 (s, 2H), 8.7 (d, 2H, J=8.0 Hz), 5.06 (m, 2H), 2.25 (m, 4H), 1.94 (m, 4H), 0.92 (t, 12H, J=7.5 Hz). $^{13}$C {$^1$H} NMR (323K): δ 163.66, 163.13, 138.25, 138.03, 132.96, 132.83, 130.18, 129.92, 129.48, 128.58, 128.49, 127.39, 123.71, 123.30, 120.77, 58.22, 25.15, 11.32, 11.19. MS 686.28 [$M^+$] (calcd 686.04). UV/vis ($CHCl_3$): $\lambda_{max}$/nm ($\epsilon/M^{-1}$ $cm^{-1}$)=526 (45 474), 490 (30 652), 458 (12 208). Fluorescence ($CHCl_3$): $\lambda_{max}$=545 nm, fluorescence quantum yield $\Phi_f$=0.81. Anal. Calcd. for $C_{34}H_{28}Br_2N_2O_4$: C, 59.32; H, 4.10; N, 4.07. Found: C, 59.23; H, 4.16; N, 4.03.

Example 3

Synthesis of dibromo-perylene-3,4:9,10-tetracarboxylic diimide derivatives

A mixture of N,N'-Bis(2,4-dimethylpent-3-yl)perylene-3,4:9,10-tetracarboxylic diimide (1a) (50 mg, 0.085 mmol) and bromine (0.935 g, 5.8 mmol) in 3 ml of dichloromethane was heated to 50° C. in a closed vial (equipped with a Teflon liner) for 1 day. The excess of bromine was removed by air bubbling and the solvent was removed under vacuum. Silica gel column chromatography using chloroform as an eluent afforded 3a (1,7-3a:1,6-3a=3:1) as an orange solid (58 mg, 92%).

A mixture of N,N'-Bis(ethylpropyl)perylene-3,4:9,10-tetra carboxylic diimide (1b) (50 mg, 0.094 mmol) and bromine (0.935 g, 5.8 mmol) in 3 ml of dichloromethane was heated to 50° C. in a closed vial (equipped with a Teflon liner) for 2 days. The excess of bromine was removed by air bubbling and the solvent was removed under vacuum. Silica gel column chromatography using chloroform as an eluent afforded 3b (1,7-3b: 1,6-3b=3:1) as a red solid (57 mg, 89%).

A mixture of perylene-diimide, N,N'-Bis(cyclohexyl) perylene-3,4:9,10-tetracarboxylic diimide (1c) (50 mg, 0.09 mmol) and bromine (0.935 g, 5.8 mmol) in 3 ml of dichloromethane was heated to 50° C. in a closed vial (equipped with a Teflon liner) for 4 days. The excess of bromine was removed by air bubbling and the solvent was removed under vacuum. Silica gel column chromatography using chloroform as an eluent afforded 3c (1,7-3c: 1,6-3c=4:1) as a red solid (55 mg, 85%).

Example 4

Synthesis of piperidinyl-N,N'-Bis(2,4-dimethyl-pent-3-yl)perylene-3,4:9,10-tetracarboxylic diimide (5)

Compound 1-bromo N,N'-Bis(2,4-dimethylpent-3-yl) perylene-3,4:9,10-tetracarboxylic diimide (2a) (100 mg, 0.15 mmol) was prepared according to Example 1, and was dissolved in 10 ml of piperidine. The solution was heated to 60° C. under dry nitrogen for 5 h with stifling. Excess of piperidine was removed under vacuum and the residue was subjected to column chromatography on silica gel using chloroform as an eluent to afford 5 (96 mg, 96%) as a green solid. $^1$H NMR: δ 9.87 (m, 1H), 8.63 (m, 6H), 4.77 (m, 2H), 3.52 (d, 2H, J=11.5 Hz), 2.97 (t, 2H, J=11.0 Hz), 2.72 (m, 4H), 1.90 (m, 6H), 1.12 (two doublets merged, 12H, J=6.5 Hz), 0.95 (two doublets merged, 12H, J=6.5 Hz). $^{13}$C {$^1$H} NMR: δ 165.54, 165.43, 165.34, 165.17, 164.43, 164.33, 164.21, 164.09, 152.69, 152.86, 152.83, 136.02, 136.00, 135.95, 135.93, 134.87, 134.85, 134.81, 134.79, 134.06, 134.03, 134.01, 133.98, 131.96, 131.52, 131.21, 130.79, 129.36, 129.16, 129.04, 129.02, 128.45, 127.07, 126.10, 126.08, 125.38, 125.36, 125.28, 124.72, 123.97, 123.94, 123.69, 123.67, 123.35, 123.32, 123.26, 123.24, 122.93, 122.91, 122.77, 122.76, 122.69, 122.67, 122.65, 122.63, 122.31, 122.29, 121.72, 121.69, 121.54, 121.51, 121.08, 121.05, 65.22, 65.04, 64.95, 64.89, 5298, 29.67, 29.14, 29.09, 25.84, 23.72, 21.87, 21.84, 21.77, 20.68, 20.66, 20.61, 20.60. MS 669.71 [M$^+$] (calcd 669.36). UV/vis (CHCl$_3$): λ$_{max}$/nm (ε/M$^{-1}$ cm$^{-1}$)=602 (18 481), 447 (14 425). Fluorescence (CHCl$_3$): λ$_{max}$=727 nm, fluorescence quantum yield Φ$_f$=0.2. Anal. Calcd. for C$_{43}$H$_{47}$N$_3$O$_4$: C, 77.10; H, 7.07; N, 6.27. Found: C, 77.11; H, 7.11; N, 6.08.

Example 5

Synthesis of piperidinyl-N,N'-Bis(2,4-dimethyl-pent-3-yl)perylene-3,4:9,10-tetracarboxylic diimide (6)

Compound 1-bromo N,N'-Bis(ethylpropyl)perylene-3,4:9,10-tetracarboxylic diimide (2b) (100 mg, 0.164 mmol) was prepared according to example 2 hereinabove, and was reacted with piperidine following the procedure analogous to the synthesis of 5 as described in Example 4 hereinabove, to afford 6 (97 mg, 96%) as a green solid. $^1$H NMR (400 MHz, CDCl$_3$, TMS): δ 9.86 (d, 1H, J=8.4 Hz), 8.60 (m, 6H), 5.10 (m, 2H), 3.50 (m, 2H), 2.97 (m, 2H), 2.30 (m, 4H), 1.82-2.0 (m, 10H), 0.95 (two triplets merged, 12H, J=7.5 Hz). $^{13}$C NMR (100 MHz, 323K): δ 164.39, 164.31, 164.18, 164.12, 152.74, 135.81, 134.77, 134.05, 131.37, 131.09, 130.96, 130.72, 130.66, 129.45, 129.14, 128.73, 128.44, 127.16, 125.76, 125.47, 124.91, 124.87, 123.92, 123.57, 123.42, 123.28, 123.20, 122.95, 121.73, 121.50, 121.30, 121.23, 57.79, 57.60, 53.01, 29.53, 25.87, 25.08, 23.72, 11.21, 11.07. MS 613.63 (calcd 613.29). UV/vis (CHCl$_3$): λ$_{max}$/nm (ε/M$^{-1}$ cm$^{-1}$)=601 (18 009), 447 (14 076). Fluorescence (CHCl$_3$): λ$_{max}$=726 nm, fluorescence quantum yield Φ$_f$=0.19. Anal. Calcd. for C$_{39}$H$_{39}$N$_3$O$_4$: C, 76.32; H, 6.40; N, 6.85. Found: C, 76.43; H, 6.52; N, 6.59.

Example 6

Synthesis of trimethylsilylacetylene-N,N'-Bis(2,4-dimethylpent-3-yl)perylene-3,4:9,10-tetracarboxylic diimide (7)

N,N'-Bis(2,4-dimethylpent-3-yl) perylene-3,4:9,10-tetracarboxylic diimide (2a) was prepared according to Example 1 hereinabove. In a glove box filled with dry nitrogen 2a (100 mg, 0.15 mmol), Pd(PPh$_3$)$_4$ (17 mg, 0.015 mmol), trimethylsilyl acetylene (22 mg, 0.22 mmol), and 2 ml of diisopropyl amine were mixed in a vial equipped with a magnetic stirrer, then CuI (1.5 mg, 0.008 mmol) was added to the mixture. The mixture was allowed to stir at room temperature overnight. The solvent was removed under vacuum and resulting mixture was subjected to silica gel chromatography using chloroform as an eluent to yield 98 mg (96%) of 7 as a red solid. $^1$H NMR: δ 10.42 (two doublets, 2H, J=8.5 Hz), 8.82 (s, 1H), 8.80 (s, 1H), 8.40 (m, 10H), 4.78 (m, 4H), 2.77 (m, 8H), 1.14 (two doublets merged, 24H, J=6.5 Hz), 0.96 (two doublets merged, 24H, J=6.5 Hz), 0.42 (s, 9H). $^{13}$C {$^1$H} NMR: δ 165.28, 165.08, 164.59, 164.16, 164.00, 163.97, 163.47, 139.35, 138.73, 134.68, 134.59, 134.54, 134.52, 134.33, 134.32, 134.30, 134.28, 133.96, 133.94, 133.90, 133.87, 131.81, 131.53, 131.46, 131.09, 130.80, 130.76, 129.08, 129.07, 128.63, 128.61, 127.23, 127.19, 127.15, 126.67, 124.04, 124.02, 123.83, 123.80, 123.50, 123.45, 123.43, 123.41, 123.21, 123.18, 123.05, 123.03, 123.01, 122.99, 122.88, 122.85, 122.55, 122.54, 121.98, 121.96, 119.96, 119.93, 119.90, 107.21, 107.15, 107.09, 105.91, 65.27, 65.25, 65.19, 65.18, 29.12, 29.10, 29.05, 29.02, 21.80, 21.76, 21.72, 20.58, 20.56, 20.51, 20.49, −0.40. MS 682.47 [M$^+$] (calcd 682.32). UV/vis (CHCl$_3$): λ$_{max}$/nm (ε/M$^{-1}$ cm$^{-1}$)=537 (66 690), 499 (39 606), 467 (14 050). Fluorescence (CHCl$_3$): λ$_{max}$=547 nm, fluorescence quantum yield Φ$_f$=0.76. Anal. Calcd. for C$_{43}$H$_{46}$N$_2$O$_4$Si: C, 75.63; H, 6.79; N, 4.10. Found: C, 75.99; H, 6.98; N, 3.82.

Example 7

Synthesis of trimethylsilylacetylene-N,N'-Bis(ethylpropyl)perylene-3,4:9,10-tetracarboxylic diimide (8)

Compound 8 was obtained as a red solid in 97% yield using procedure analogous to the one used for the synthesis of 7. $^1$H NMR: δ 10.15 (d, 1H, J=8.0 Hz), 8.32-8.63 (m, 6H), 5.06 (m, 2H), 2.27 (m, 4H), 1.98 (m, 4H), 0.98 (m, 12H), 0.45 (s, 9H). $^{13}$C NMR (323K): δ 164.33, 164.12, 163.62, 138.94, 134.79, 134.74, 134.43, 134.08, 131.30, 131.01, 130.92, 129.37, 128.91, 127.46, 127.39, 127.35, 126.98, 124.22, 124.00, 123.63, 123.43, 122.97, 122.72, 120.17, 107.33, 106.28, 58.16, 58.07, 25.29, 25.23, 11.30, 11.26, −0.34. MS 626.70 [M$^+$] (calcd 626.26) (UV/vis (CHCl$_3$): λ$_{max}$/nm (ε/M$^{-1}$ cm$^{-1}$)=537 (60 348), 499 (35 877), 467 (12 743), 433 (5 562). Fluorescence (CHCl$_3$): λ$_{max}$=546 nm, fluorescence quantum yield Φ$_f$=0.76. Anal. Calcd. for C$_{39}$H$_{38}$N$_2$O$_4$Si: C, 74.73; H, 6.11; N, 4.47. Found: C, 74.45; H, 6.27; N, 4.10.

Example 8

Synthesis of 1-piperazinyl N,N'-Bis(2,4-dimethyl-pent-3-yl) perylene-3,4:9,10-tetracarboxylic diimide (9)

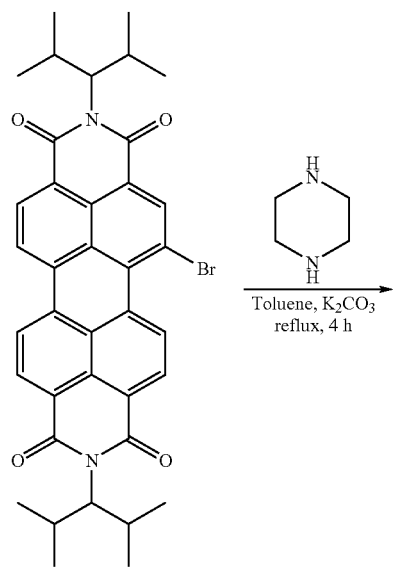

Piperazine (1 g, 11.6 mol) in 15 ml of toluene was taken in a round bottom flask and immersed into oil bath at 60° C. with stifling for 30 min. Then 1-bromo-N,N'-Bis(2,4-dimethyl-pent-3-yl)perylene diimide (2a) (400 mg, 0.6 mmol) and 400 mg (2.9 mmol) of anhydrous potassium carbonate were added into the reaction mixture. The reaction was continued for 10 h. After removing the toluene by vacuum evaporation, the remaining residue was taken in dichloromethane and extracted with distilled water. The organic layer was separated and dried over anhydrous $Na_2SO_4$. The solvent was removed under vacuum and the mixture was subjected to silica gel column chromatography. The first band, unreacted starting material, was collected by chloroform elution and then green colour product was collected by to chloroform: methanol (9:1) mixture to yield 220 mg (54%) the mono piperazine derivative as a dark-green solid. $^1$HNMR (500 NMR, $CDCl_3$, TMS): δ 10.00 (two doublets merged, 1H, J=8 Hz), 8.5-8.7 (m, 6H), 4.75 (m, 2H), 3.52 (m, 2H), 3.0-3.2 (m, 5H), 2.63-2.75 (m, 6H), 1.12 (two doublets merged, 12H, J=6.5 Hz), 0.93 (two doublets merged, 12H, J=6.5 Hz). $^{13}$C NMR (500 NMR, $CDCl_3$, TMS): δ 165.49, 165.37, 165.24, 165.19, 164.38, 164.27, 164.11, 151.90, 135.75, 135.72, 135.68, 135.66, 134.80, 134.77, 134.74, 134.72, 134.11, 134.09, 134.06, 131.91, 131.62, 131.16, 130.90, 129.43, 129.33, 129.02, 128.73, 127.12, 125.53, 125.49, 125.14, 124.82, 124.10, 124.08, 123.81, 123.49, 123.47, 123.32, 123.30, 123.13, 123.09, 123.04, 122.71, 122.69, 122.43, 122.41, 121.95, 121.92, 121.76, 121.32, 121.29, 65.26, 65.09, 65.00, 64.96, 51.44, 51.28, 29.14, 29.10, 21.88, 21.79, 20.67, 20.61. MS 671.94 [M+1] (calcd 671.36). UV/vis ($CHCl_3$): $\lambda_{max}$/nm ($\epsilon$/L $mol^{-1}$ $cm^{-1}$)=588 (18 629), 446 (12 163). Fluorescence ($CHCl_3$): $\lambda_{max}$=705 nm, fluorescence quantum yield $\Phi_f$=0.3. Anal. Calcd for $C_{42}H_{46}N_4O_4$:

Example 9

Synthesis of 1-piperazinyl N,N'-Bis(ethyl propyl)perylene-3,4:9,10-tetracarboxylic diimide (10)

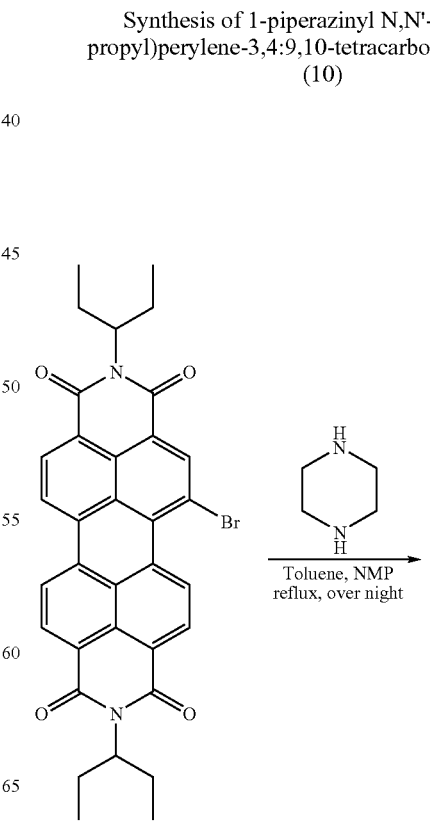

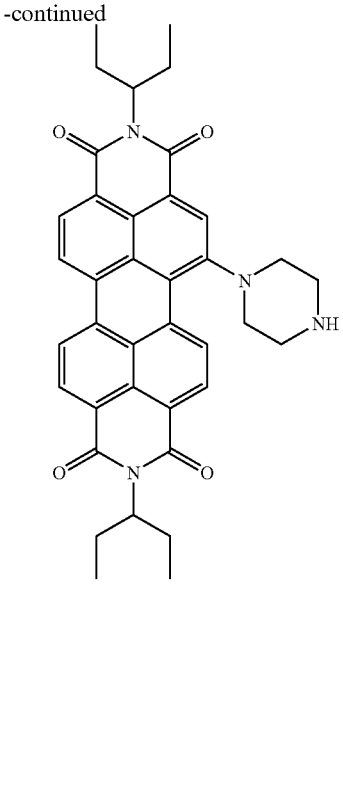

Piperazine (1 g, 11.6 mol) in 15 ml of toluene was taken in 50 ml round bottom flask under nitrogen and immersed into oil bath at 60° C. with stirring for 30 min 1-bromo-N,N'-Bis (ethyl propyl) perylene diimide (2b) (100 mg, 0.188 mmol) was added and reaction was for 2 days. After removing the toluene by vacuum, the remaining residue was taken in dichloromethane (100 ml) and extracted with distilled water (2×100 ml). The organic layer was separated and dried over anhydrous Na$_2$SO$_4$. The solvent was removed under vacuum and the mixture was subjected to silica gel column chromatography. The first band, unreacted starting material was collected by chloroform elution and then green colour product was collected by chloroform:methanol (9.5:0.5) mixture to yield 70 mg (60%) the mono piperazine derivative. $^1$HNMR (400 NMR, CDCl$_3$, TMS): δ 10.00 (d, 1H, J=7 Hz), 8.54-8.67 (m, 6H), 5.1 (m, 2H), 3.47 (d, 2H, J=12 Hz), 3.23 (t, 2H, J=10 Hz), 3.15 (d, 2H, J=12 Hz), 3.06 (t, 2H, J=10 Hz), 2.29 (m, 4H), 1.96 (m, 4H), 0.94 (t, 12H, J=7.2 Hz). $^{13}$C NMR (400 NMR, CDCl$_3$, TMS): δ 164.33, 164.23, 164.08, 152.07, 135.25, 131.04, 129.42, 129.13, 127.18, 125.66, 125.24, 125.20, 125.05, 124.06, 123.63, 123.53, 123.42, 123.32, 123.23, 123.04, 122.00, 121.66, 121.60, 121.48, 57.83, 57.63, 52.71, 45.85, 25.06, 11.18, 11.12. MS 615.82 [M+1] (calcd [M] 614.73). UV/vis (CHCl$_3$): λ$_{max}$/nm (ϵ/L mol$^{-1}$ cm$^{-1}$)=585 (22 419), 446 (15 567). Fluorescence (CHCl$_3$): λ$_{max}$=712 nm, fluorescence quantum yield Φ$_f$=0.23.

Example 10

Synthesis of 4-amino phenyl acetylene N,N'-Bis(ethyl propyl)perylene-3,4:9,10-tetracarboxylic diimide (11)

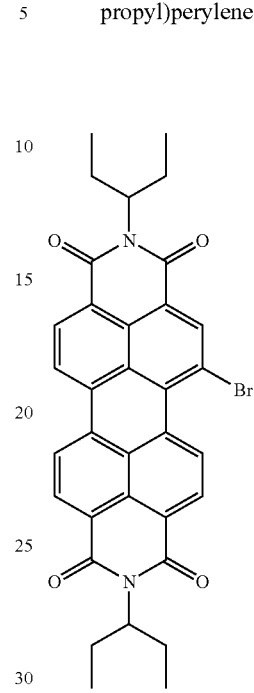
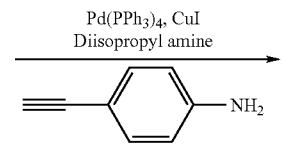
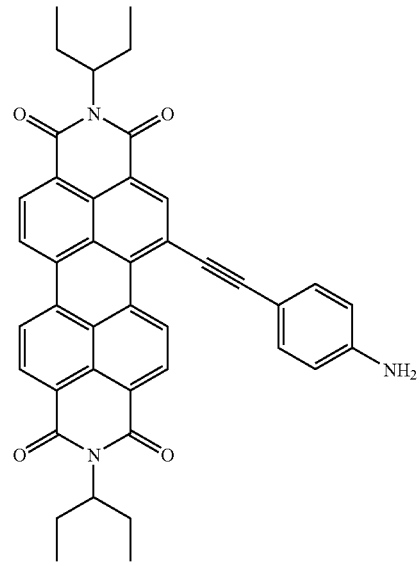

Sonogashira coupling. 100 mg of Monobrominated PDI-2b, 5 mol % of Pd(PPh$_3$)$_4$, 1 eq. of 4-ethenyl aniline were taken in a vial with magnetic stirrer, then 2 ml of diisopropyl amine was added followed by 5 mol % of CuI. The mixture was allowed to stir at room temperature overnight. The TLC showed the formation of product with dark brown colour. The product was purified by silica gel chromatography using chloroform as an eluent. The yield is quantitative.

Figure 9:
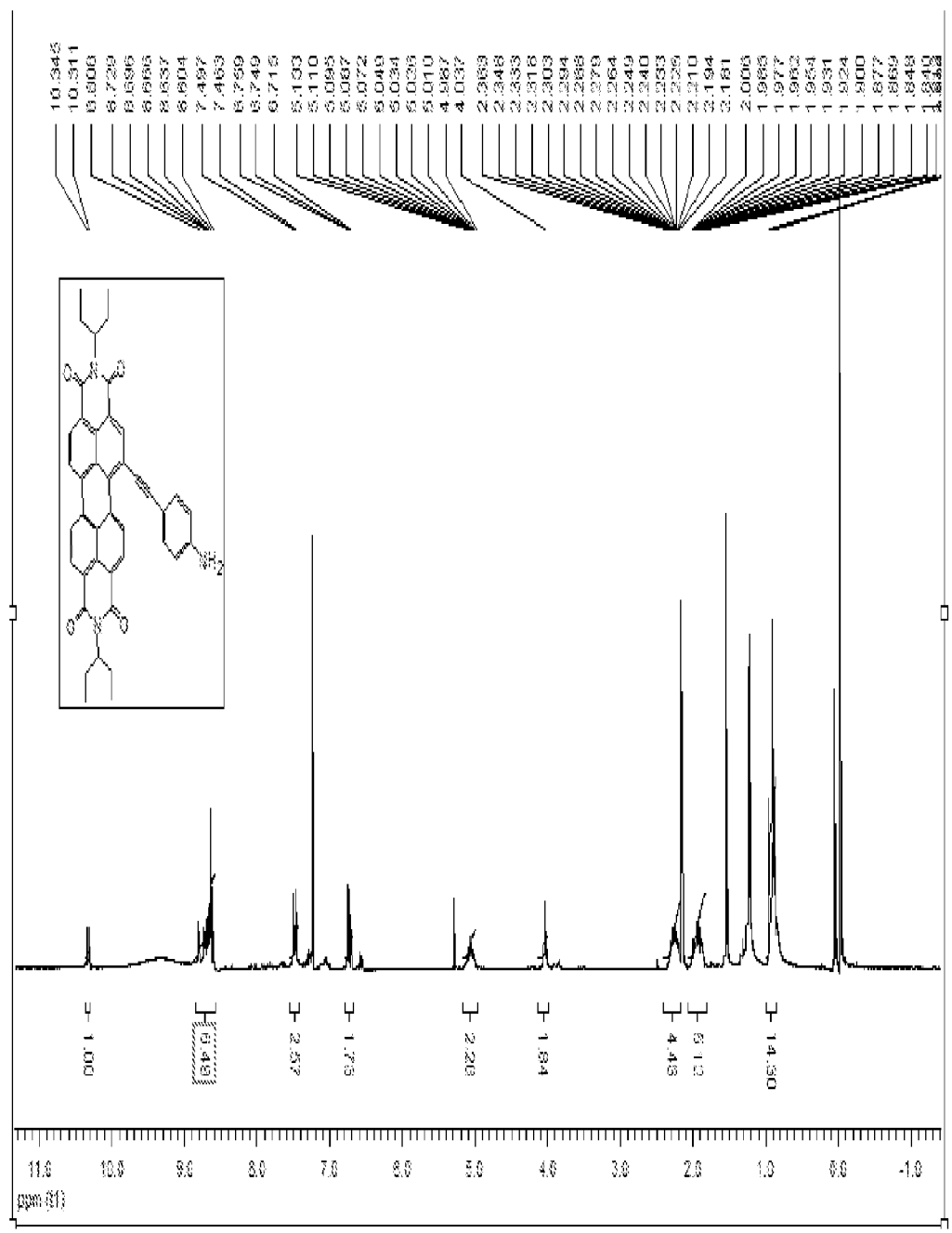
FIG. 9 depicts $^1$H NMR spectra of compound of formula 11.

The $^1$HNMR (400 NMR, CDCl$_3$, TMS) of compound of formula 11 is depicted in FIG. 9.

Example 11

Synthesis of 4-amino phenyl acetylene N,N'-Bis(2,4-dimethyl-pent-3-yl)perylene-3,4:9,10-tetracarboxylic diimide (12)

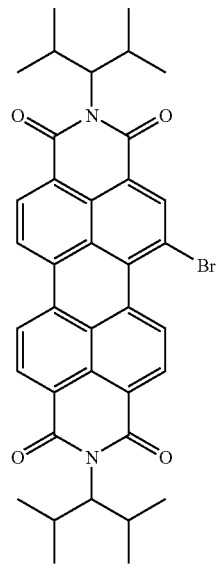

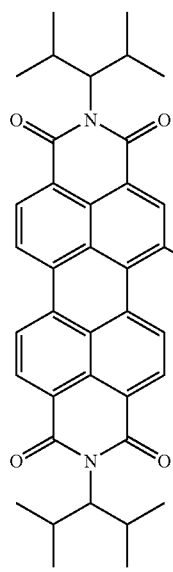

Sonogashira coupling. 100 mg of 2a, 5 mol % of Pd(PPh$_3$)$_4$, 1 eq. of 4-ethenyl aniline were taken in a vial with magnetic stirrer, then 2 ml of diisopropyl amine was added followed by 5 mol % of CuI. The mixture was allowed to stir at room temperature overnight. The TLC showed the formation of product with dark brown colour. The product was purified by silica gel chromatography using chloroform as an eluent. The yield is quantitative.

Figure 10:
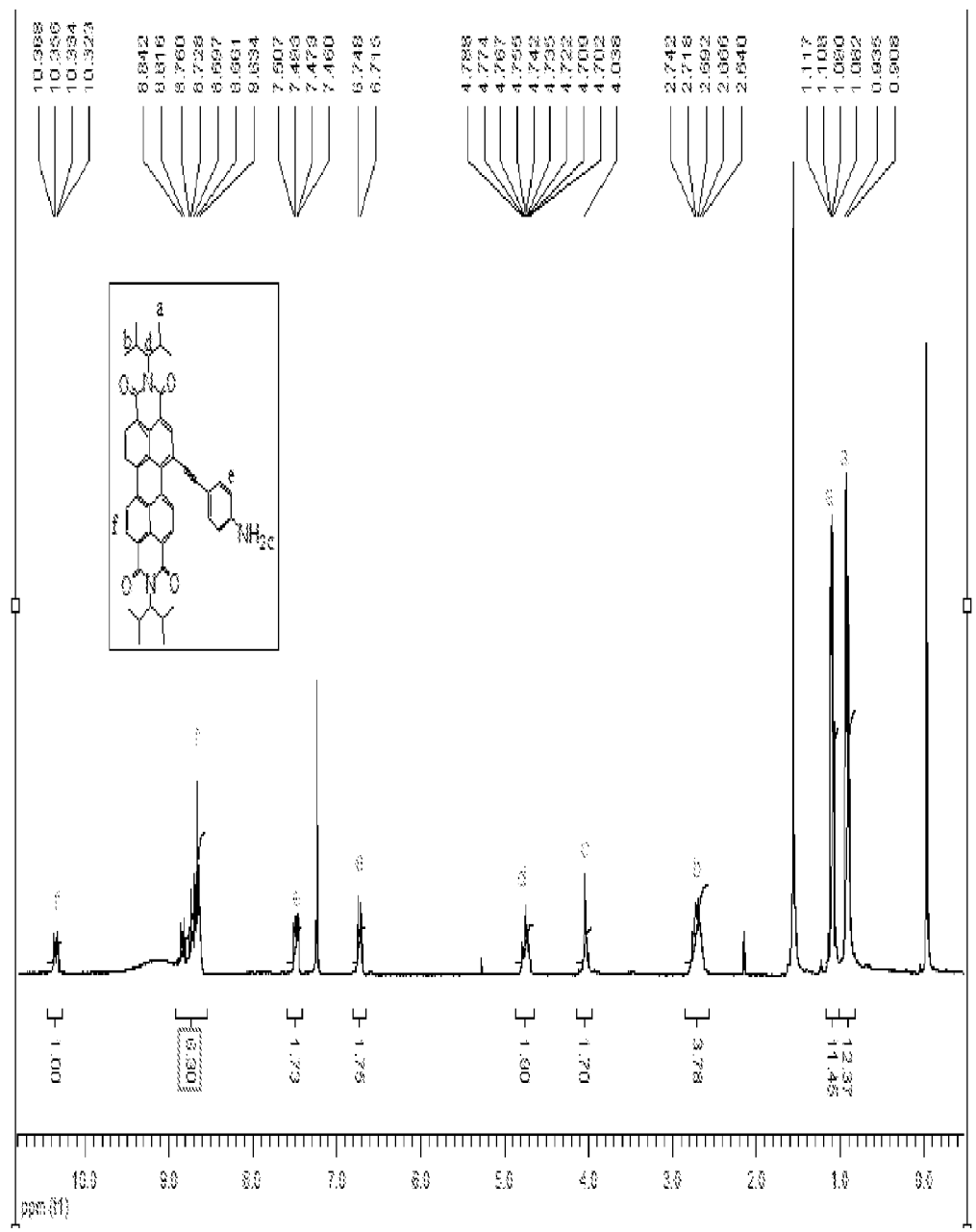
FIG. 10 depicts $^1$H NMR spectra of compound of formula 12.

The $^1$HNMR (400 NMR, CDCl$_3$, TMS) of compound of formula 12 is depicted in FIG. 10.

Example 12

Synthesis of N-isonicotinoyl 1-piperazinyl N,N'-Bis (2,4-dimethyl-pent-3-yl)perylene-3,4:9,10-tetracarboxylic diimide (13) name.

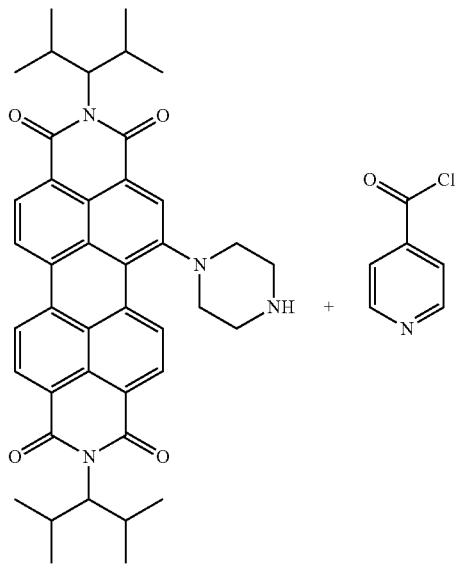

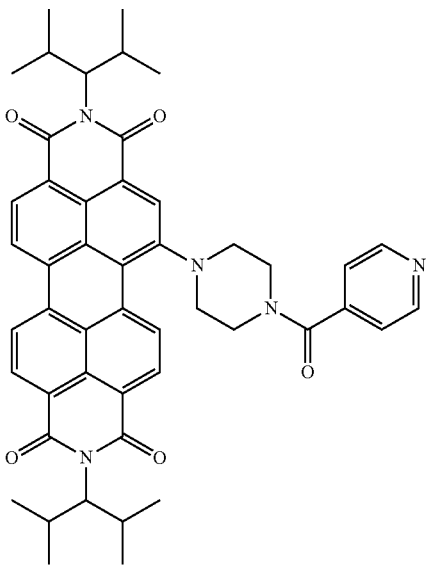

Mixture of equivalent amounts in dichloromethane. The residue after removing solvent was subjected to silica gel column chromatography first using dichloromethane as an eluent and then with 2% of ethanol in dichloromethane. Purple colour band was collected. The $^1$H NMR showed the formation of desired product.

Figure 11:
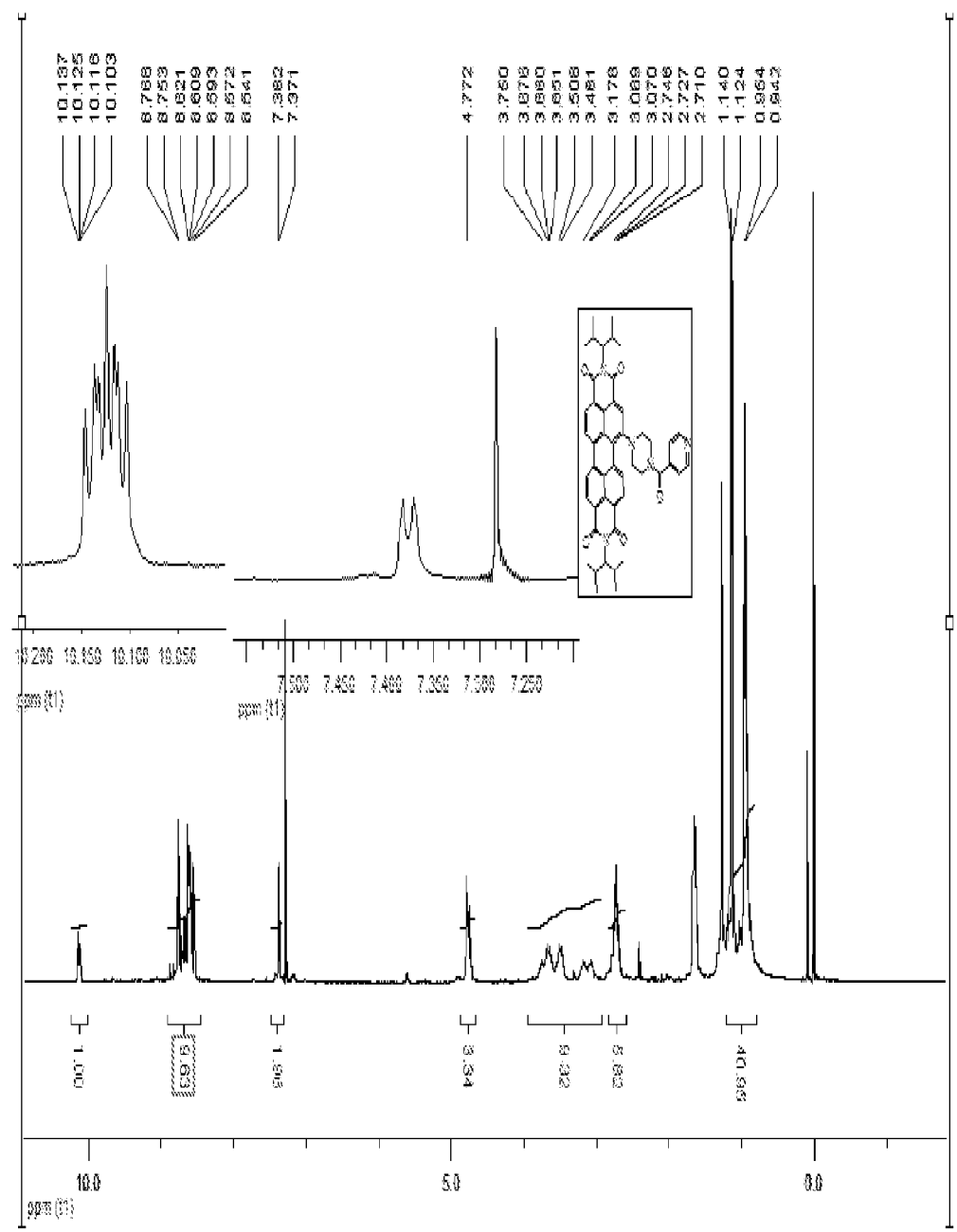
FIG. 11 depicts $^1$H NMR spectra of compound of formula 13.

The $^1$H NMR (400 NMR, CDCl$_3$, TMS) of compound of formula 13 is depicted in FIG. 11.

Example 13

Synthesis of 4-ethynyl phenyl acetylene N,N'-Bis(ethyl propyl) perylene-3,4:9,10-tetracarboxylic diimide (14)

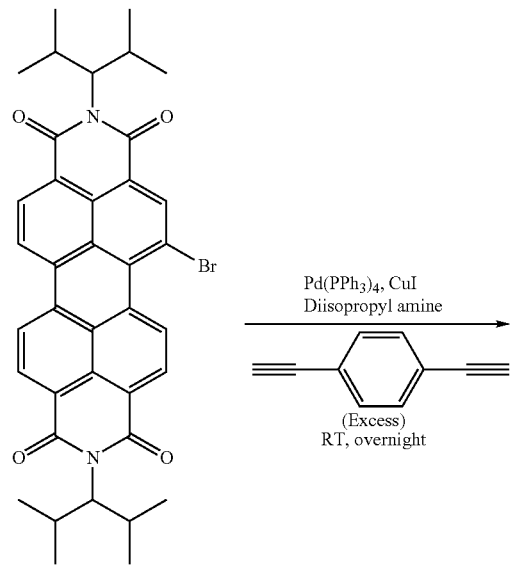

Sonogashira coupling (analogous to Example 11). The reaction was stopped after 3 h to prevent the formation of self coupling between alkynes. CuI can be replaced with $ZnBr_2$.

Figure 12:
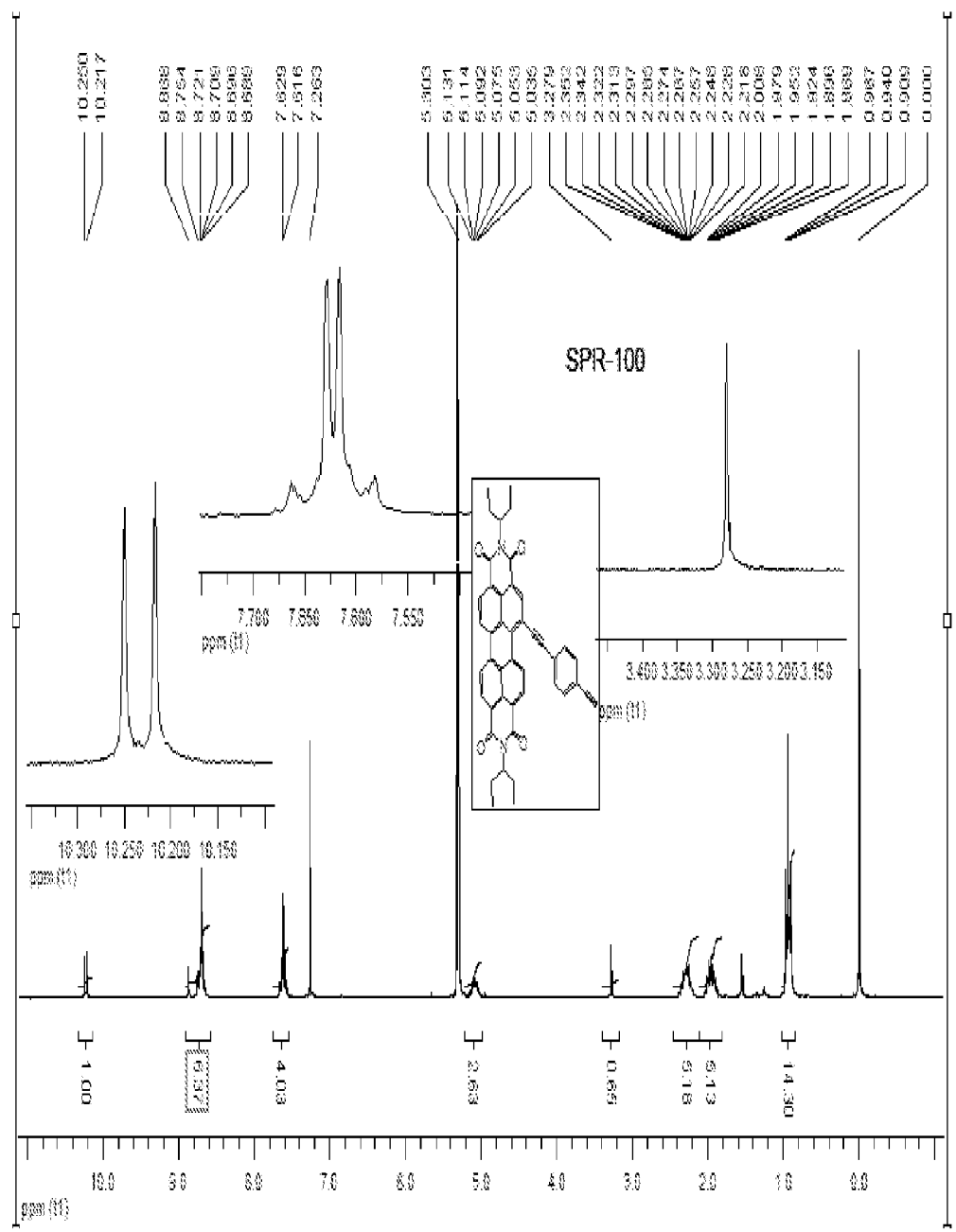
FIG. 12 depicts $^1$H NMR spectra of compound of formula 14.

The $^1$HNMR (400 NMR, $CDCl_3$, TMS) of compound of formula 14 is depicted in FIG. 12.

Example 14

Synthesis of 1-ethynyl N,N'-Bis(ethyl propyl)perylene-3,4:9,10-tetracarboxylic diimide (15)

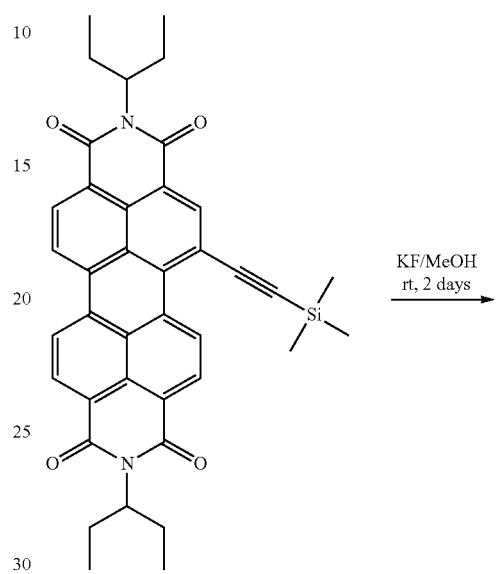

Starting material 5b (50 mg) in dichloromethane (10 ml) and KF (20 mg) mixed in MeOH (3 ml). It was allowed to stir at RT for 2 days to get complete deprotection. Care should be taken while adding MeOH in such a way that PDI derivative does not precipitate. After workup with water to remove KF and evaporation of solvent, the mixture was subjected for column chromatography using chloroform as an eluent to yield the product (80%).

Example 15

Synthesis of Compound of (2,2'-bipyridine)-5-N,N'-Bis(ethyl propyl) perylene-3,4:9,10-tetracarboxylic diimide (16)

Example 16

Synthesis of 1-(N,N'-Bis(ethyl propyl)perylene-3,4:9,10-tetracarboxylic diimide) 4-acetylene phenyl ethynyl)-7-piperidinyl N,N'-Bis(ethyl propyl) perylene-3,4:9,10-tetracarboxylic diimide (17)

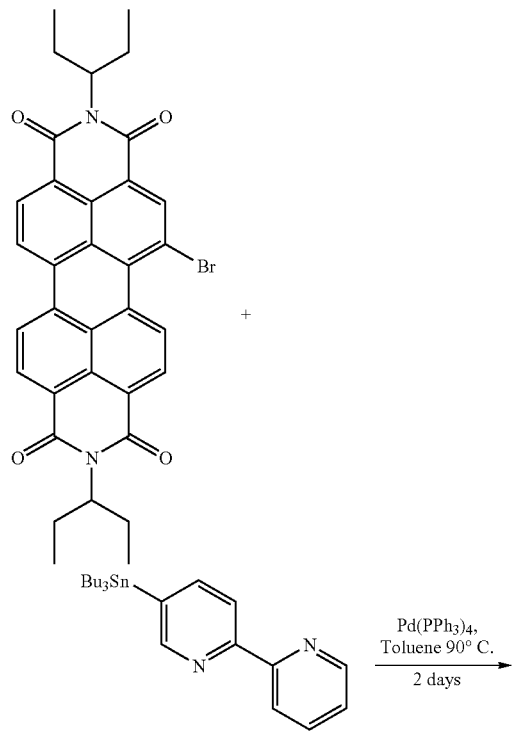

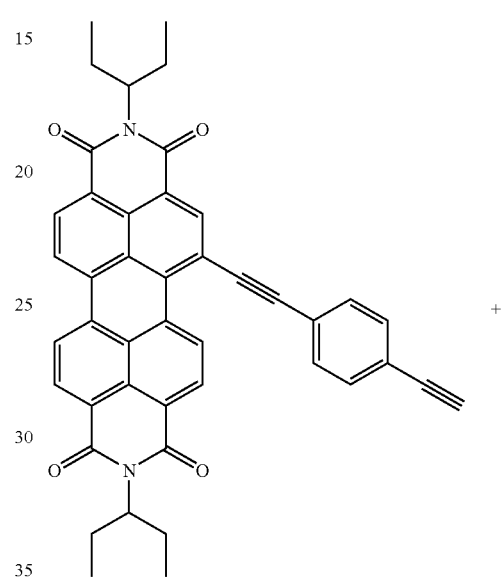

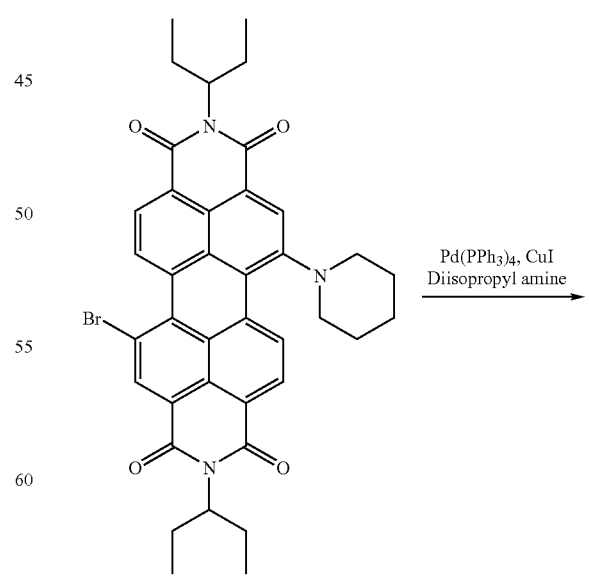

Reflux in toluene (in a closed vial—taken inside clove box) for two days. Product (yield 20%) was separated through preparative TLC using dichloromethane as an eluent.

Figure 13:
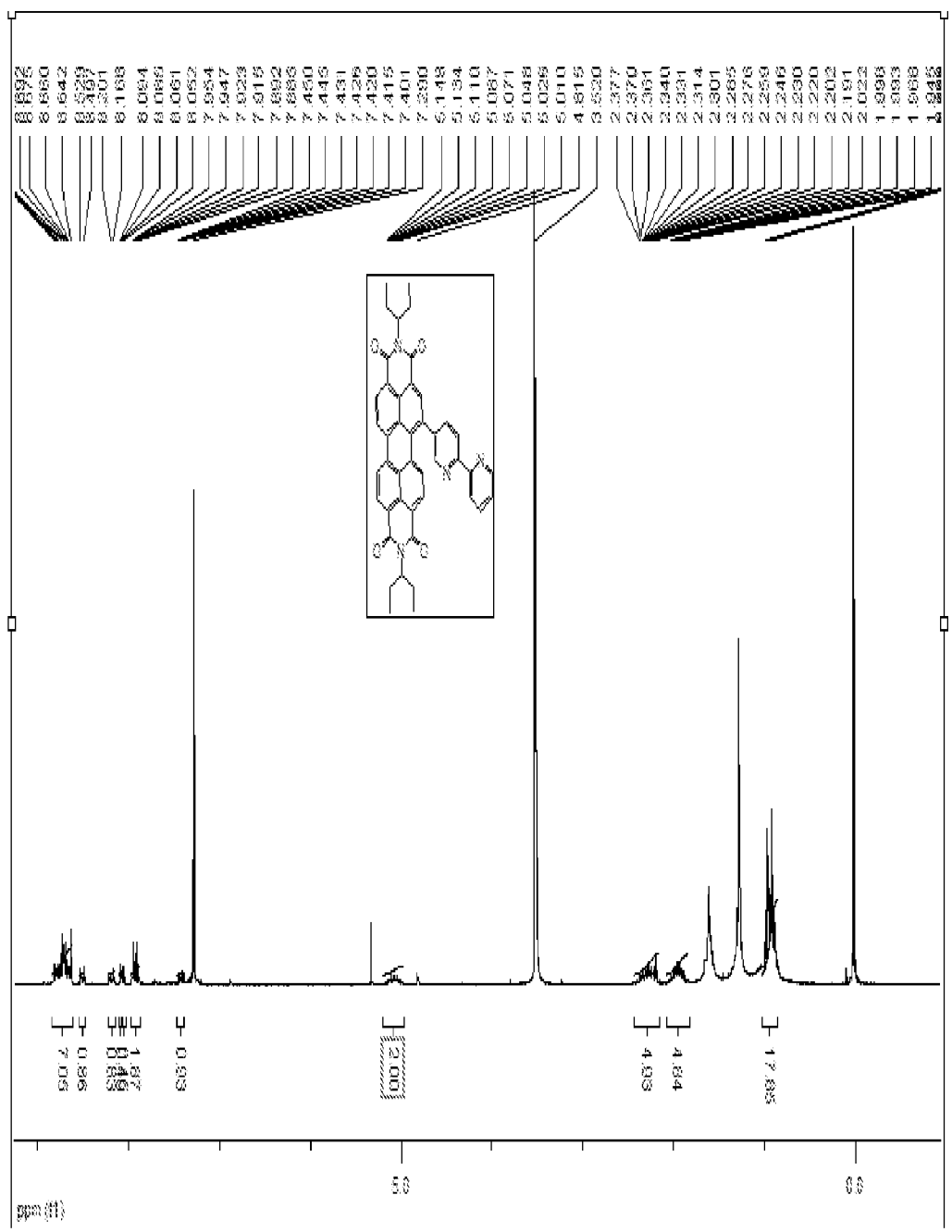
FIG. 13. depicts $^1$H NMR spectra of compound of formula 16.

The $^1$HNMR (400 NMR, CDCl$_3$, TMS) of compound of formula 16 is depicted in FIG. 13.

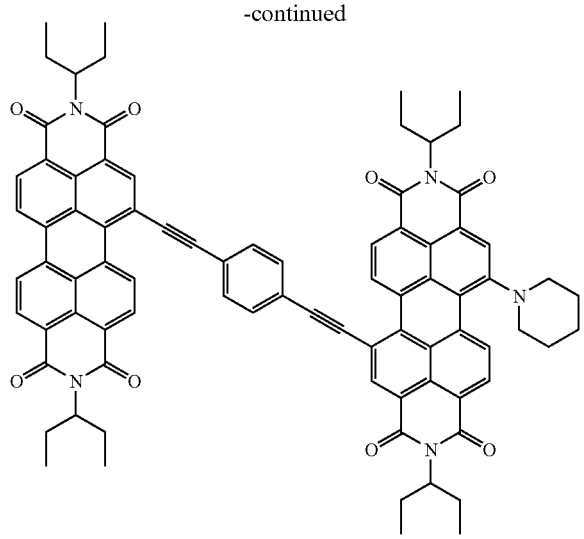

Compound of formula 17 was prepared using sonogashira coupling procedure used in the above examples. Compound of formula 17 was purified through silica gel column chromatography using chloroform as eluent.

Figure 14:
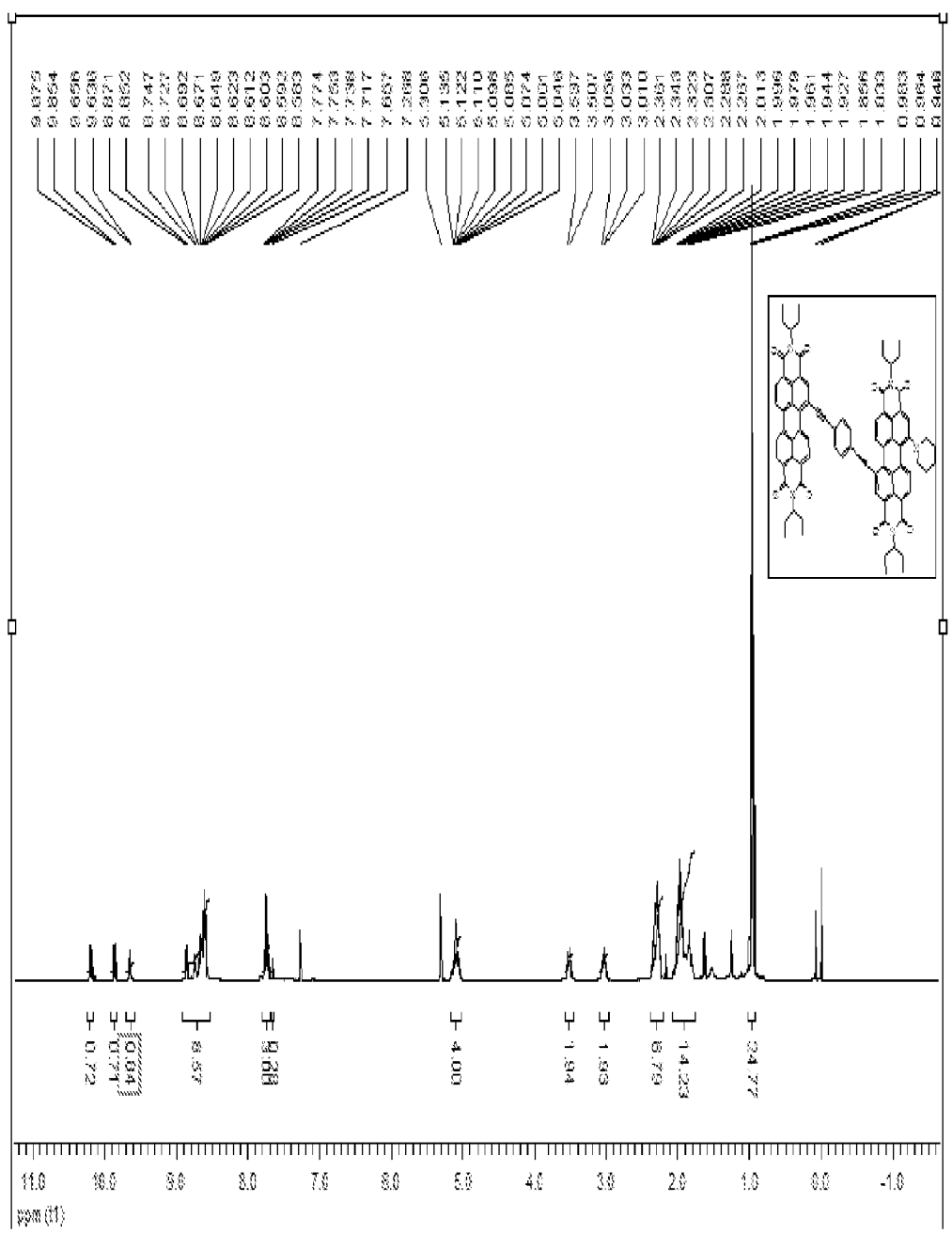
FIG. 14. depicts $^1$H NMR spectra of compound of formula 17.

The $^1$HNMR (400 NMR, CDCl$_3$, TMS) of compound of formula 17 is depicted in FIG. 14.

Example 17

Photophysical and Redox Properties of Compounds 2-8

Photophysical and redox properties of monobrominated PDI derivatives 2a,b are similar to those of dibrominated 3a,b. The latter are very similar to the reported photophysical and redox characteristics of 1,7-dibromo-PDIs. Monopiperidine PDI derivatives 5 and 6 show absorption and emission that is less red-shifted than the one observed for disubstituted piperidine derivatives (absorption maximum at 680 nm, emission at 770 nm) as expected for lower electron-donating ability of one piperidine group vs. two such groups. The emission quantum yields (0.2) are identical for compounds 5 and 6 and 1,7-dipiperidine PDI derivative.

TABLE 1

Absorption and emission properties of compounds 2-8 in chloroform, and redox potentials in dichloromethane (in V vs SCE)$^a$

| Compound | absorption $\lambda_{max}^b$ ($\epsilon$)$^c$ | emission $\lambda_{em}^b$ ($\lambda_{ex}$)$^b$ | Φ | $^1E_{1/2}^{RED}$ | $^2E_{1/2}^{RED}$ | $E_{1/2}^{OX}$ |
|---|---|---|---|---|---|---|
| 2a | 524 (74669) | 538 (488) | 0.92 | −0.59 | −0.80 | |
| 2b | 524 (61578) | 537 (488) | 0.88 | −0.59 | −0.79 | |
| 1,7-3a | 526 (49825) | 545 (490) | 0.82 | −0.52 | −0.73 | |
| 1,7-3b | 526 (45474) | 545 (490) | 0.81 | −0.54 | −0.76 | |
| 5 | 602 (18481) | 727 (600) | 0.20 | −0.66 | −0.86 | 1.06 |
| 6 | 601 (18009) | 726 (600) | 0.19 | −0.74 | −0.93 | 1.06 |
| 7 | 537 (66690) | 547 (493) | 0.76 | −0.61 | −0.81 | |
| 8 | 537 (60348) | 546 (493) | 0.76 | −0.60 | −0.80 | |

$^a$All measurements were performed at room temperature;
$^b$in nm;
$^c$in M$^{-1}$ cm$^{-1}$.

Example 18

X-Ray Analysis of 1,7-dibromo-N,N'-Bis(ethylpropyl)perylene-3,4:9,10-tetracarboxylic diimide (1,7-3b)

Figure 5:
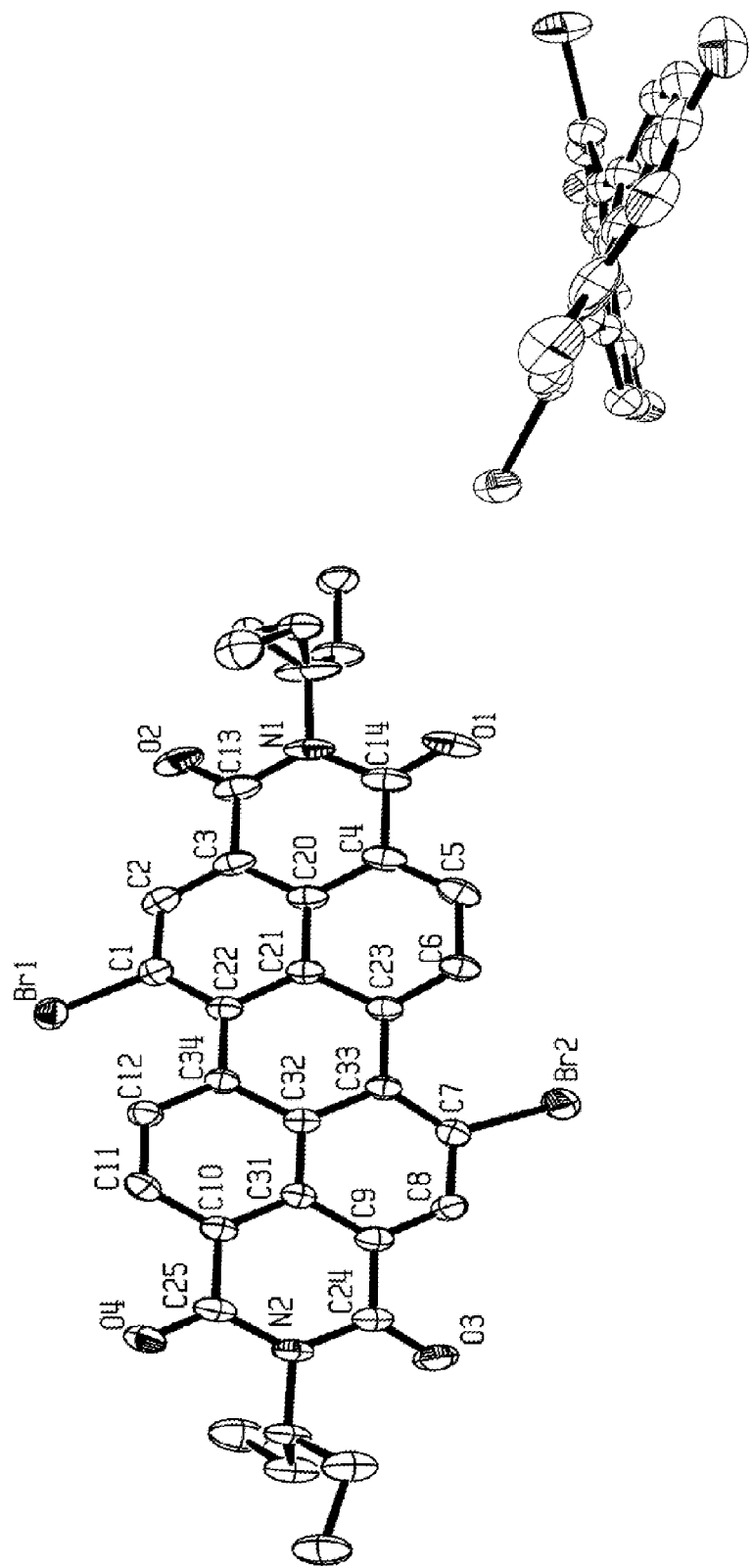
FIG. 5 depicts ORTEP drawing of structure of 1,7-3b (left, 50% probability, hydrogens are omitted for clarity) and view along the N-N axis showing twisted perylene backbone (right, 50% probability, alkyl groups at imide nitrogens and all hydrogens are omitted for clarity). There is a minor disorder in one of the ethylpropyl groups. Selected bond lengths (Å): Br1-C1, 1.905 (4); C1-C2, 1.402 (5); C2-C3, 1.375 (6); C3-C13, 1.486 (5); C13-N1, 1.395 (6); C13-O2, 1.225 (6); C3-C20, 1.406 (6); C20-C21, 1.423 (5); C21-C22, 1.434 (5); C22-C1, 1.403 (5); C22-C34, 1.468 (5).
Figure 6:
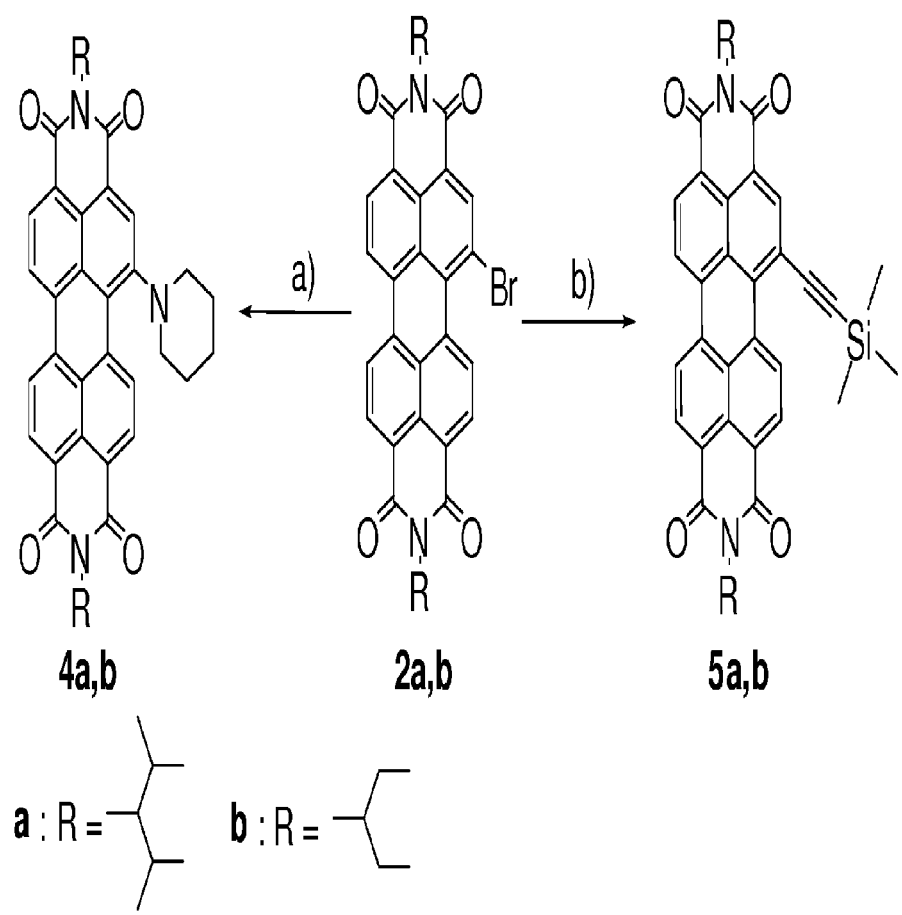
FIG. 6 is a synthetic scheme for the preparation of compounds of formula 5, 6, 7 and 8 providing the reagents and conditions for the different regioisomers (a) piperidine, 60° C., N2, 5 h, 96% of 5 and 96% of 6; (b) Pd(PPh$_3$)$_4$ (10 mol %), CuI (5 mol %), trimethylsilyl acetylene, diisopropylamine, rt, 96% of 7 and 97% of 8.

The structure of 1,7-3b was further elucidated by X-ray crystallography. Single crystals of 1,7-3b suitable for X-ray analysis were grown from dichloromethane/hexane solution. The central six-membered ring was twisted (FIG. 5) with dihedral angles of 23.3° and 21° associated with bay area carbon atoms C1-C22-C34-C12 and C6-C23-C33-C7 respectively, these values being similar the core twist angle of 24° in N,N'-dicyclohexyl-1,7-dibromo PDI.

Example 19

Computational Methods

All calculations were carried out using Density Functional Theory (DFT) as implemented in Gaussian 03 program (Frisch, M. J.; Trucks, G. W. et al; Gaussian, Inc., Wallingford Conn. 2004. Geometry optimizations for minima were carried out using the standard Schlegel algorithm (Peng, C.; Ayala, P. Y.; Schlegel, H. B.; Frisch, M. J. *J. Comput. Chem.* 1996, 17, 49. or Schlegel, H. B. *J. Comput. Chem.* 1982, 3, 214) in redundant internal coordinates until in the neighborhood of the solution, and then continued using analytical second derivatives. Optimizations for transition states were carried out with an initial guess for the transition state being generated from manual manipulation of the geometry using MOLDEN (Schaftenaar, G.; Noordik, J. H. *J. Comput.-Aided Mol. Design.* 2000, 14, 123-129). Geometries were optimized using the default pruned (75,302) grid, or when necessary for conversion with the "ultrafine" grid, i.e., a pruned (99,590) grid.

The B3LYP exchange correlation functional (three-parameter hybrid density functional method) (Becke, A. D. *J. Chem. Phys.* 1993, 98, 5648-5652. Stevens, P. J.; and Devlin, F. J.; Chabalowski, C. F.; Frisch, M. J. *J. Phys. Chem.* 1994, 98, 11623) was employed together with two basis sets. The first, D95V, is the Huzinaga-Dunning double-ζ basis set (Dunning Jr., T. H.; Hay, P. J. *Modern Theoretical Chemistry*; Plenum: New York, 1976; Vol. 3) and the second, cc-pVDZ, is the Dunning correlation-consistent polarized valence double-basis set (Dunning Jr., T. H. *J. Chem. Phys.* 1989, 90, 1007-1023). Geometry optimizations were carried out using the former basis set while the energetics of the reaction were calculated at these geometries with the latter basis set, to increase the accuracy of the results. Zero-point and RRHO (rigid rotor-harmonic oscillator) thermal corrections were obtained from the unscaled computed frequencies.

Results

DFT calculations at the B3LYP/cc-pVDZ//B3LYP/D95V level of theory were performed for the following PDI derivatives:

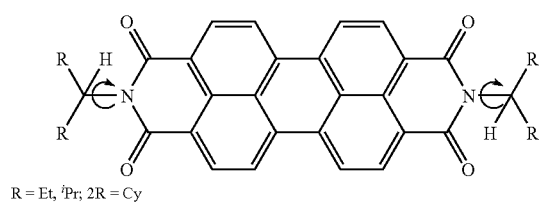

R = Et, $^i$Pr; 2R = Cy

Figure 7A:
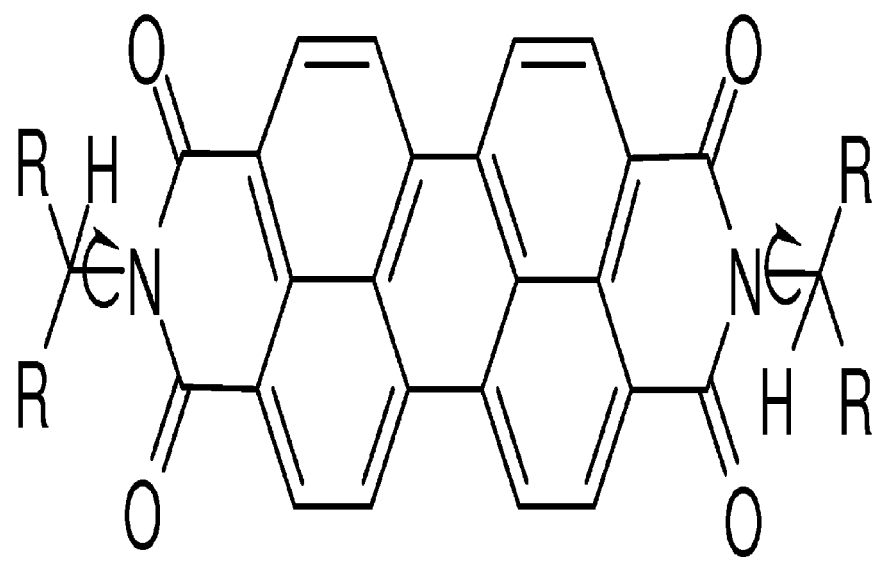
FIG. 7A-B depicts computed structures for rotational isomers and the transition states for imide group rotation. Hydrogens (except for NCHR$_2$) are omitted for clarity.
Figure 7B:
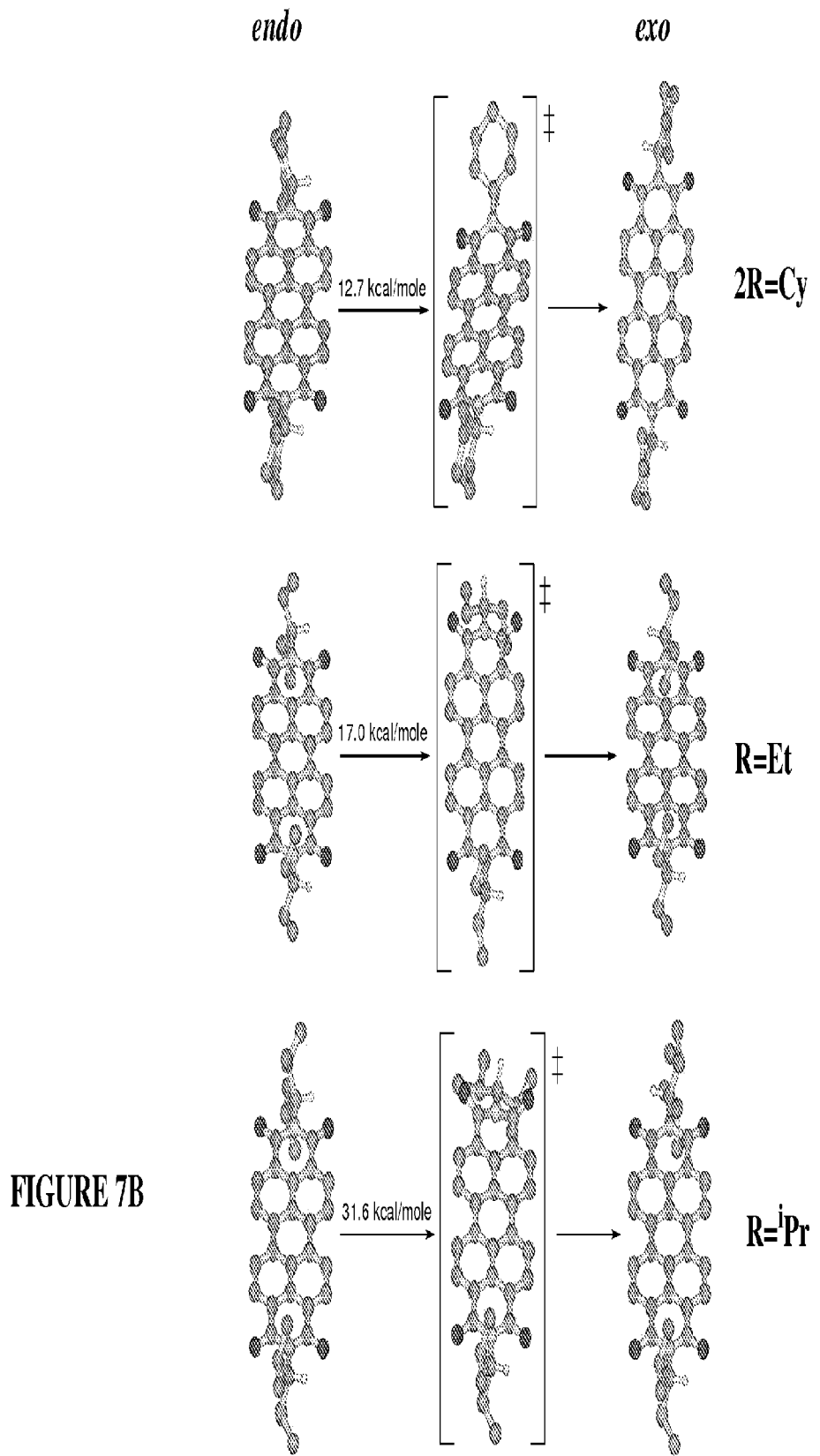

For each compound two isomers were located: exo, where the N—CHR$_2$ hydrogen atoms are pointing to the opposite directions and endo, where they point to the same direction as depicted in FIG. 7. For each isomer couple the transition state for the rotation around the N—C(sp$^3$) bond was located (FIG. 7). The rotation barriers around the N—CHR$_2$ bonds corresponded well to the steric bulk of the imide substituents: 12.7 kcal/mol for 2R=Cy, 17.0 kcal/mol for R=Et, and 31.6 kcal/mol for R=$^i$Pr. These findings showed that the rotation around the N—C bond for 2R=Cy and R=Et can occur at room temperature, while the rotation around the N—C bond for R=$^i$Pr was restricted due to larger steric bulk of dimethylpenthyl group. The rotation around the N—C bond for R=Et (rotation time of ca. 300 msec as estimated from the kinetic barrier) was comparable to the NMR time scale, which is in agreement with slight broadening of the $^1$H and $^{13}$C NMR signals of 2b-6. The rotational barriers of the brominated PDI derivatives were similar to the nonbrominated molecules. Thus, for monobrominated PDI with R=$^i$Pr, the N—C rotation barrier was found to be 32.8 kcal/mol, and for the 1,7-dibrominated PDI with R=$^i$Pr the barrier for rotation is 32.5 kcal/mol.

Figure 8A:
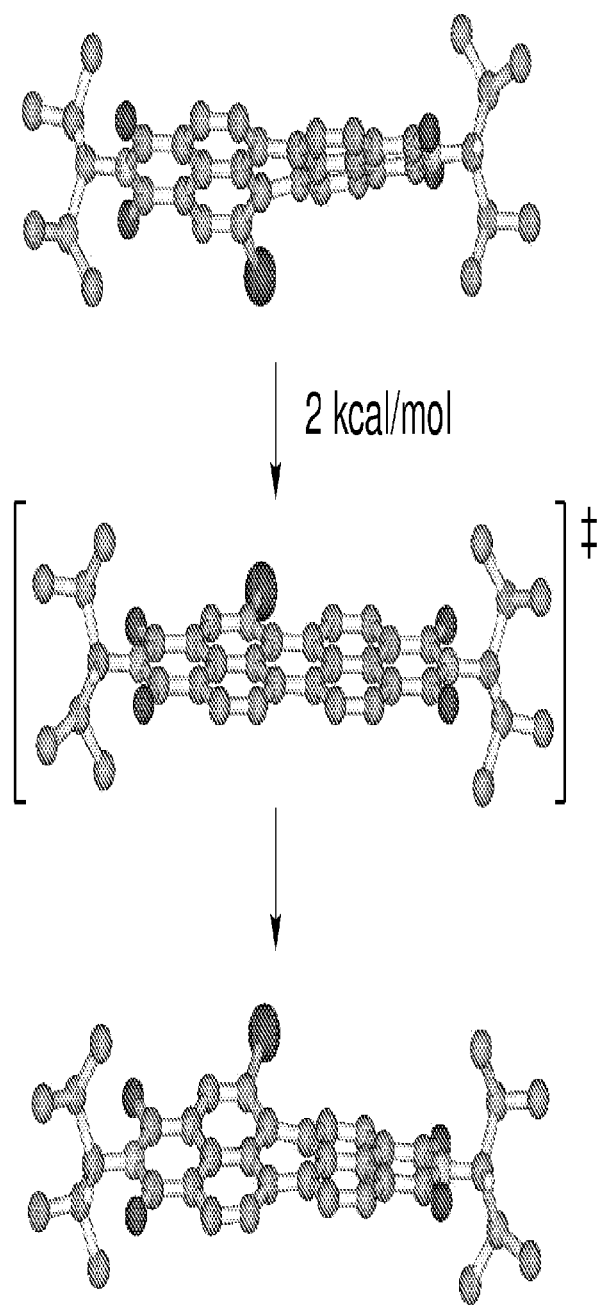
FIG. 8 depicts computed structures for rotational isomers and the transition states for core twist in monobromo-PDI (FIG. 8A); and core twist in dibromo-PDI.
(FIG. 8B).
Figure 8B:
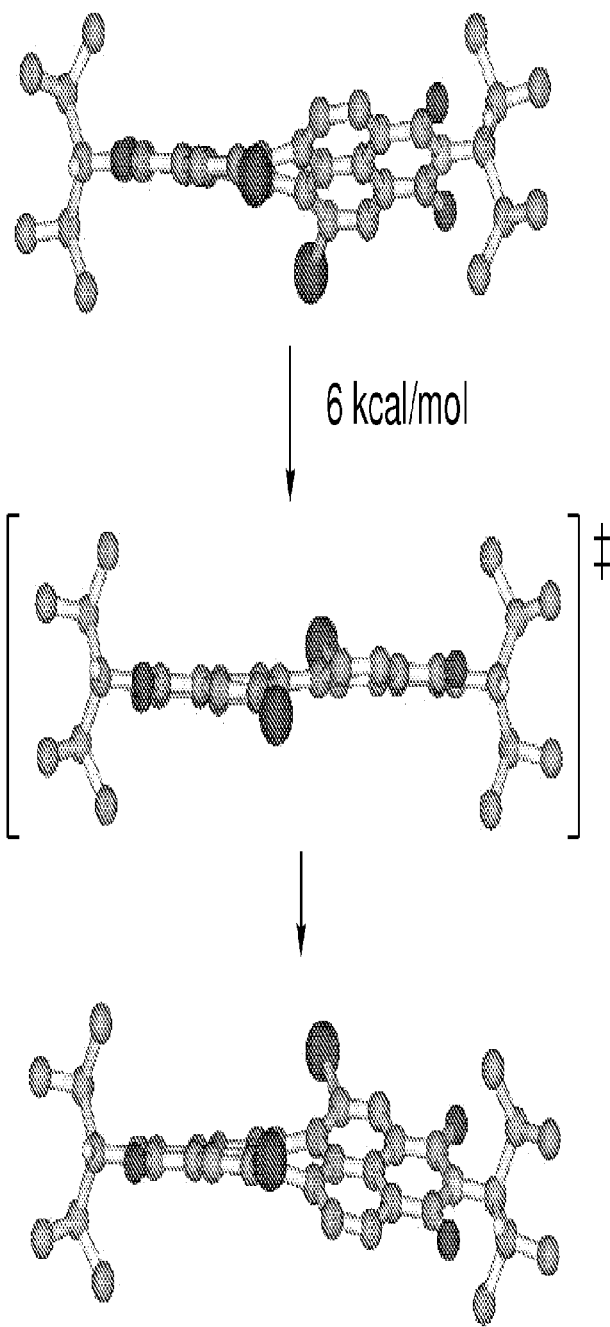

The motion associated with the PDI core twist, was addressed and the PDI-Br-2a (where R=$^i$Pr) (FIG. 8A) was analyzed. The PDI skeleton was twisted, for the congested bay region. The barrier for the PDI aromatic core twisting (FIG. 8A) was found to be rather low, 2 kcal/mol, therefore, core twist is expected to be facile. Accordingly, no additional isomers were expected to be observed as a result of PDI bromination. Similar results were obtained for the PDI derivative with two Br atoms (compound 3a). Core twist barrier for this case was found to require a slightly higher energy of 6 kcal/mol (FIG. 8B).

Example 21

Synthesis of Compound (18)

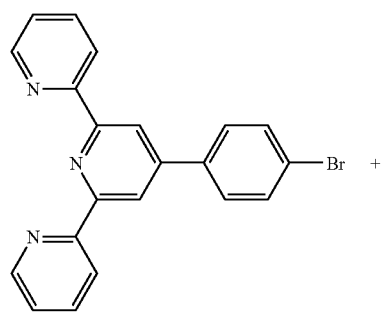

18

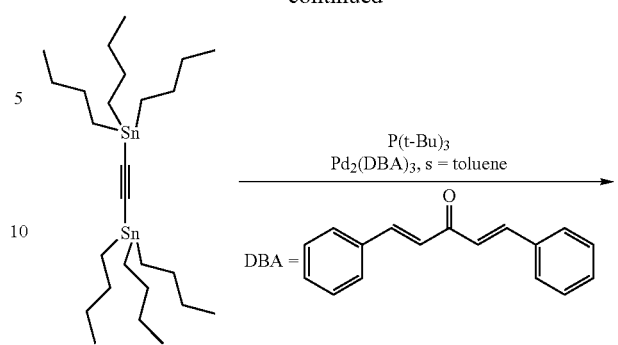

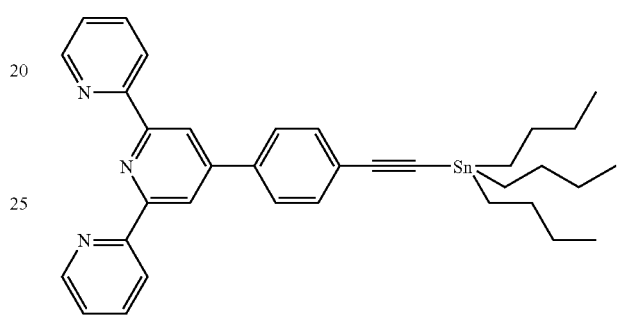

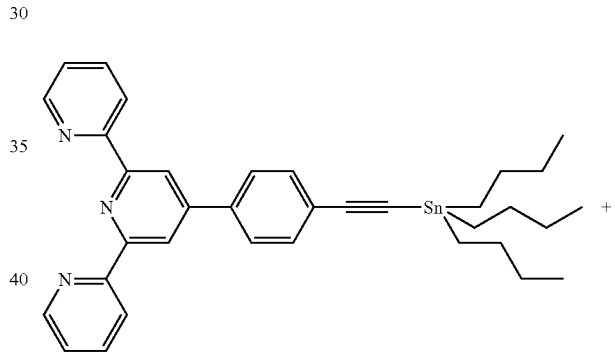

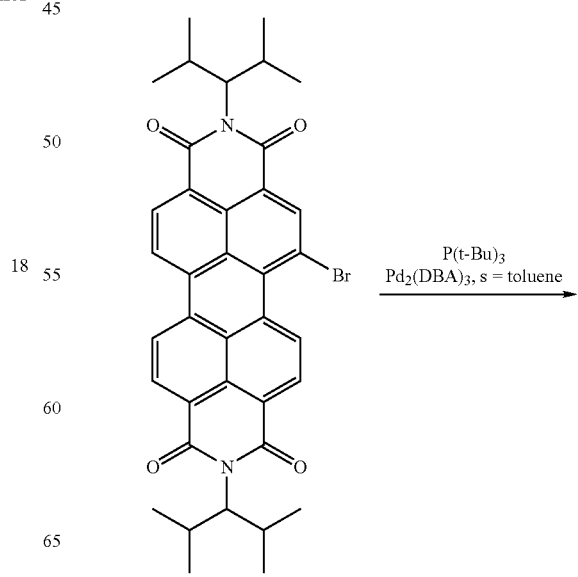

-continued

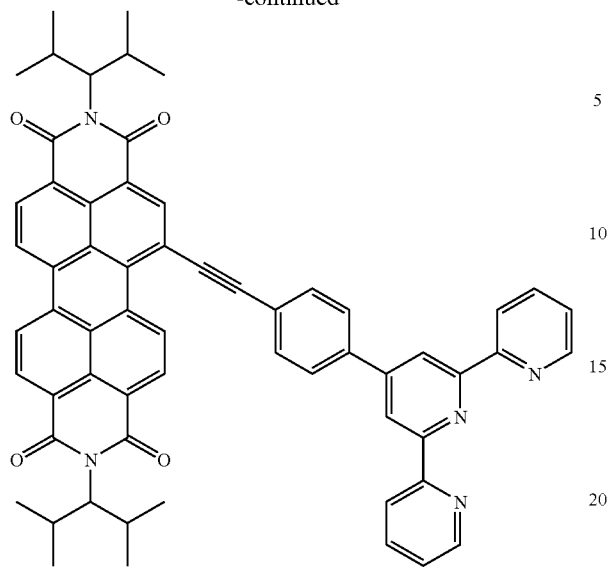

The coupling reaction was carried out in the glove box under N$_2$ atmosphere.

Figure 15:
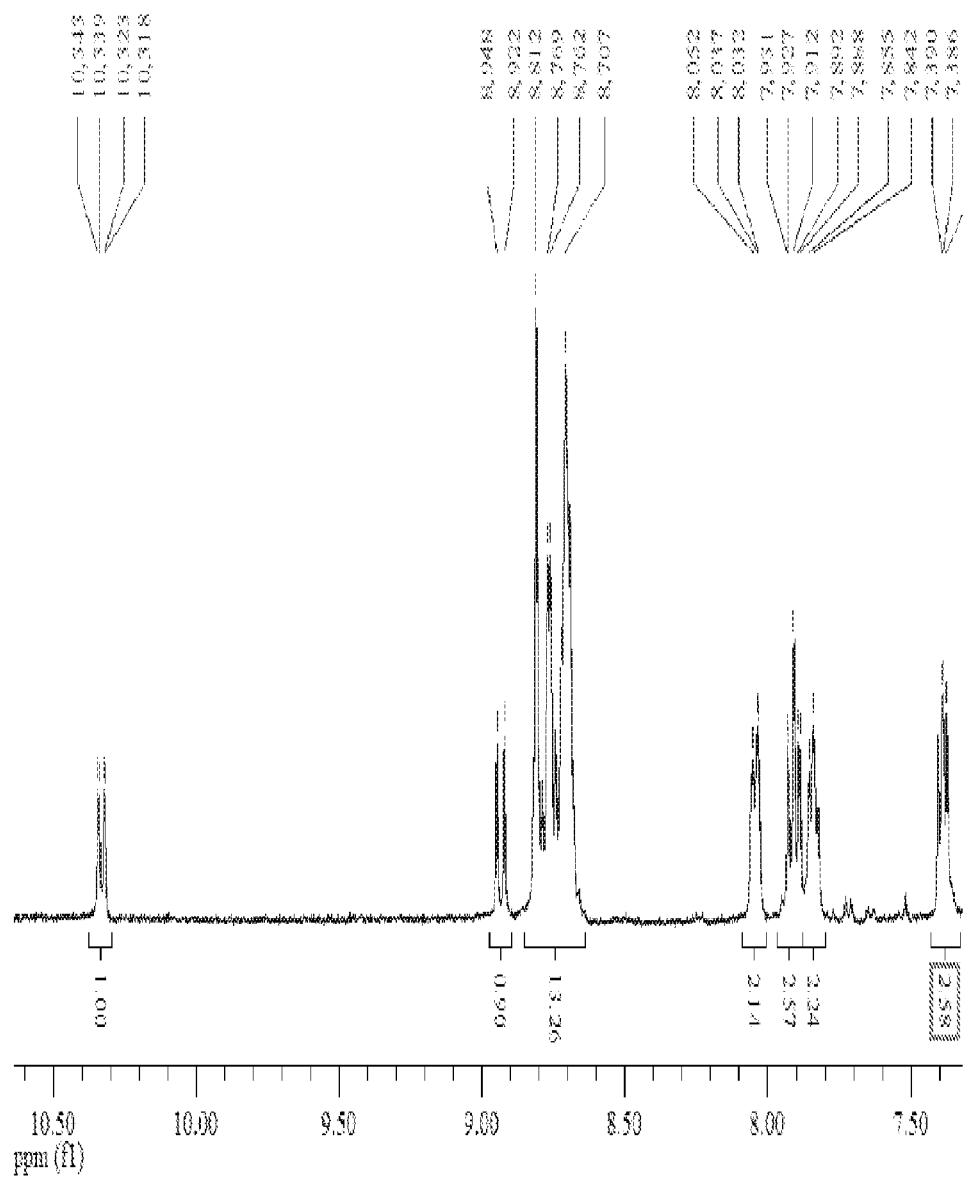
FIG. 15. depicts $^1$H NMR spectra of compound of formula 18.

Inside the glove box, 130 mg of PDI-Br (1 eq, Mw=665.62 gr/mole, n=1.95×10$^{-4}$ mole) were weighed in a clean vial. 14.65 mg of Pd$_2$(DBA)$_3$, (0.05 eq) (10% mole, Mw=915.72 gr/mole, n=1.6×10$^{-5}$ mole) & 10% mole of tri-(t-Butyl)phosphine (6.75 mg, Mw=211.3902 gr/mole) were added to PDI-Br dissolved in 10 ml of toluene. The mixture was stirred for 5 min & then added dropwise to a toluenic solution of Terpy-acetylene-tributylTin. According to the TLC, the reaction is completed in 2 h. Silica gel column chromatography resulted in 231 mg (Mw=918.09 gr/mole) of the product, Terpy-PDI (dmp), 84% yield. Mass-spectra and NMR confirm that the product was obtained as presented in FIG. 15.

Example 21

Synthesis of Compound (19)

19

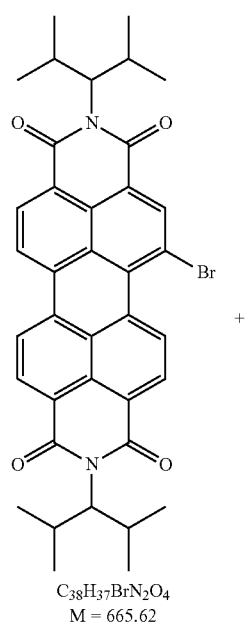

-continued

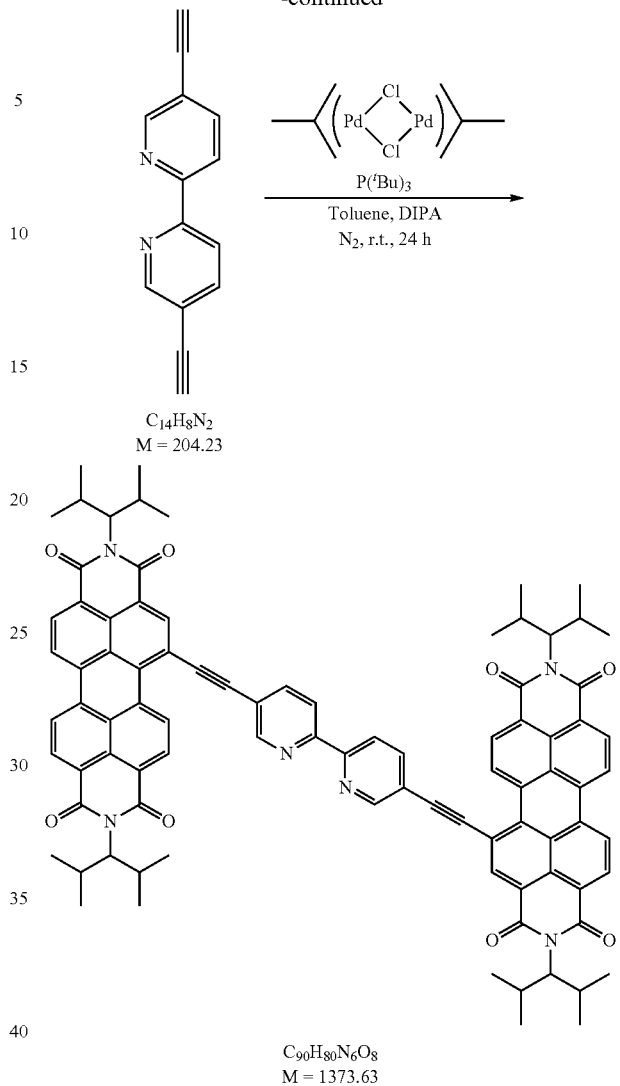

The coupling reaction was carried out in the glove box under N$_2$ atmosphere.

To a stirred solution of 30 mg (45 μmol) of monobromo-PDI in toluene (1 mL) was added a solution of 0.886 mg (2.25 μmol) Allylpalladium-chloride-dimer and 0.910 mg (4.5 μmol) P($^t$Bu)$_3$ in 145 μL THF. Subsequently, diisopropylamine (0.75 μL) was added, followed by the dropwise addition of a solution of 3 mg (15 μmol) 5,5'-DiEthynyl-2,2'-Bipyridine in toluene (0.5 mL). The dark-red solution was stirred overnight. During that time, the solution became darker and a dark-red solid precipitated.

After the reaction was finished (checked by TLC) the solvent was evaporated in high vacuum and the product purified using silica column chromatography (eluent: CHCl$_3$/MeOH (MeOH gradient 1%-2%), silica 40-63 μm). For further purification, all solvents were evaporated from the product fraction; the resulting solid was dissolved in a minimum amount of CHCl$_3$, precipitated in acetone and centrifuged. The precipitate was washed 4× with acetone and dried in the vacuum.

Figure 16:
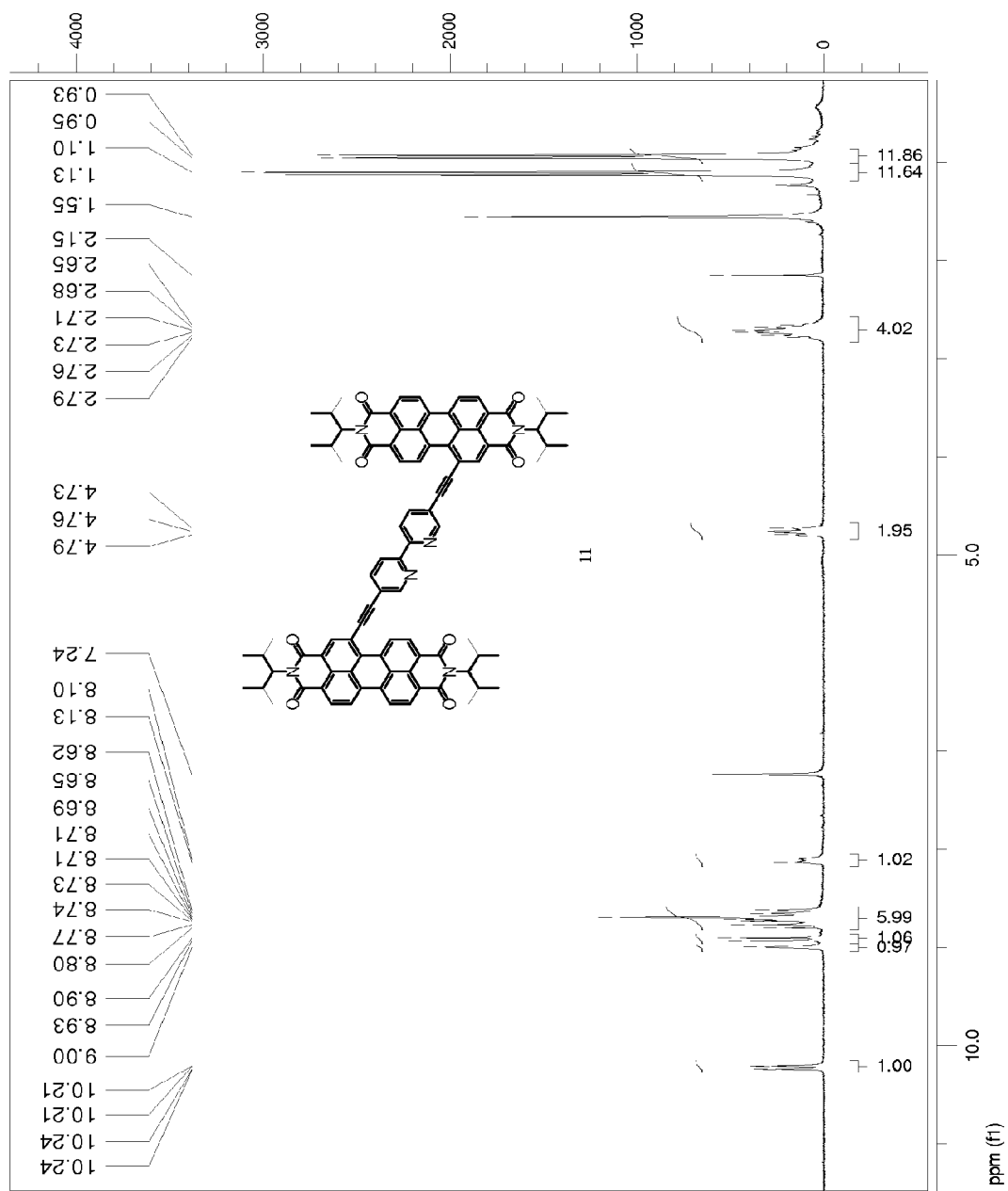
FIG. 16 depicts $^1$H NMR spectra of compound of formula 19.

Yield: 11 mg (8 μmol, 53% with respect to 5,5'-DiEthynyl-2,2'-Bipyridine used). Mass-spectra are consistent with the structure. The product was characterized by NMR as presented in FIG. 16.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A process for the preparation of dibrominated perylene diimide compound represented by the structures of formula 1,6-3 and 1,7-3;

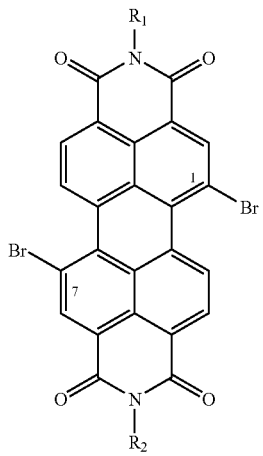

1,7-3

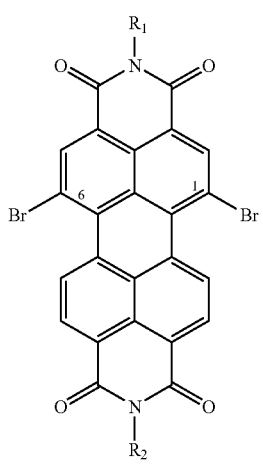

1,6-3 wherein $R_1$ and $R_2$ are the same or different substituted or unsubstituted linear or branched alkyl group, substituted or unsubstituted saturated carbocyclic or heterocyclic ring or aryl;

comprising the steps of
a) brominating compound of formula 1

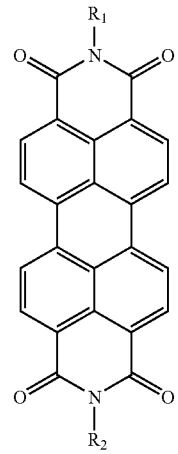

1 wherein $R_1$ and $R_2$ are as defined above;
in the presence of bromine and a chlorinated solvent at reflux for a period of time sufficient to obtain a mixture comprising compounds of formula 1,6-3 and 1,7-3; and
b) separating between 1,6-3 and 1,7-3 regioisomer compounds by recrystallizing compound of formula 1,7-3 yielding crystalline pure perylenediimide of formula 1,7-3, thereby separating between said regioisomer compounds.

2. The process of claim 1, wherein $R_1$ and $R_2$ are the same or different dimethylpentyl, tertbutyl, ethylpropyl, linear alkyl ($C_1$-$C_{12}$), or cyclohexane.

3. The process of claim 1, wherein said chlorinated solvent is dichloromethane, chloroform, or chlorinated aliphatic solvent.

4. The process of claim 1, wherein said period of time is between 1-4 days.

5. The process of claim 1, wherein said period of time is between 24-48 h.

6. The process of claim 1, wherein said recrystallization is from dichloromethane/hexane mixture (v/v, 1:1).

7. A process for the preparation of dibrominated perylene-diimide and monobrominated perylene-diimide compounds represented by the structures of formula 2, 1,6-3 and 1,7-3;

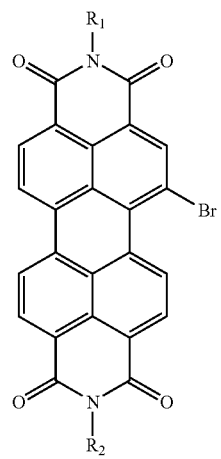

2

1,7-3

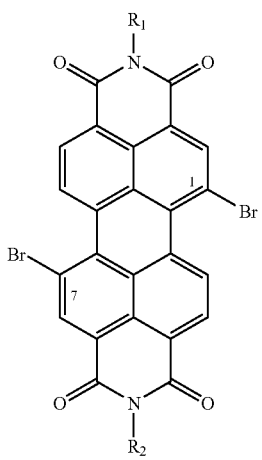

1,6-3

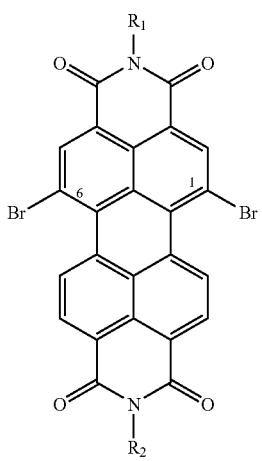

wherein $R_1$ and $R_2$ are the same or different substituted or unsubstituted linear or branched alkyl group, substituted or unsubstituted saturated carbocyclic or heterocyclic ring or aryl;

comprising the steps of
a) brominating compound of formula 1

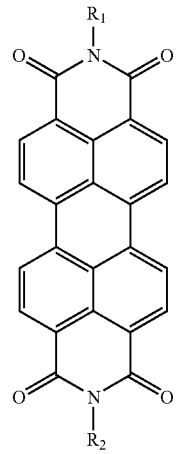

wherein $R_1$ and $R_2$ are as defined above;
in the presence of bromine and a chlorinated solvent at a temperature range of between about 15-30° C. for a period of time sufficient to obtain a mixture comprising compound of formula 2, 1,6-3 and 1,7-3;
b) isolating compound of formula 2 by chromatography; and
c) separating between 1,6-3 and 1,7-3 regioisomer compounds by recrystallizing compound of formula 1,7-3 yielding crystalline pure perylene-diimide of formula 1,7-3, thereby separating between said two regioisomer compounds.

8. The process of claim 7, wherein $R_1$ and $R_2$ are the same or different dimethylpentyl, tertbutyl, ethylpropyl, linear alkyl ($C_1$-$C_{12}$), or cyclohexane.

9. The process of claim 7, wherein said chlorinated solvent is dichloromethane, chloroform, or chlorinated aliphatic solvent.

10. The process of claim 7, wherein said period of time is between 1-4 days.

11. The process of claim 10, wherein said period of time is between 3-4 days.

12. The process of claim 7, wherein said temperature range is between 22-24° C.

* * * * *

UNITED STATES PATENT AND TRADEMARK OFFICE
CERTIFICATE OF CORRECTION

PATENT NO. : 8,399,670 B2 Page 1 of 1
APPLICATION NO. : 12/599292
DATED : March 19, 2013
INVENTOR(S) : Rybtchinski et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 590 days.

Signed and Sealed this
First Day of September, 2015

Michelle K. Lee
*Director of the United States Patent and Trademark Office*